United States Patent
Begovich et al.

(10) Patent No.: US 11,505,830 B2
(45) Date of Patent: Nov. 22, 2022

(54) MULTIPLEX PCR DETECTION OF ALK, RET, AND ROS FUSIONS

(71) Applicant: Roche Molecular Systems, Inc., Pleasanton, CA (US)

(72) Inventors: Ann Begovich, El Cerrito, CA (US); Cindy Cheung, Fremont, CA (US); Javelin Chi, Pleasanton, CA (US); Grantland Hillman, Oakland, CA (US); Dwight Kuo, Castro Valley, CA (US); Michael Lee, San Ramon, CA (US); Chitra Manohar, San Ramon, CA (US); Xiaoju Max Ma, San Carlos, CA (US); Ellen Ordinario, Oakland, CA (US); Jaya Rajamani, Pleasanton, CA (US); Huan Truong, Milpitas, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/993,375

(22) Filed: May 30, 2018

(65) Prior Publication Data

US 2018/0346994 A1 Dec. 6, 2018

Related U.S. Application Data

(60) Provisional application No. 62/513,226, filed on May 31, 2017.

(51) Int. Cl.
*C12Q 1/6886* (2018.01)
*C12Q 1/6851* (2018.01)
*C12Q 1/686* (2018.01)

(52) U.S. Cl.
CPC ......... *C12Q 1/6886* (2013.01); *C12Q 1/6851* (2013.01); *C12Q 1/686* (2013.01); *C12Q 2537/143* (2013.01); *C12Q 2600/112* (2013.01); *C12Q 2600/118* (2013.01); *C12Q 2600/156* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | | | |
|---|---|---|---|---|
| 2009/0156475 A1* | 6/2009 | Rikova | ........ | C07K 14/47 435/194 |
| 2013/0059762 A1* | 3/2013 | Leamon | ........ | C12Q 1/6806 506/26 |
| 2013/0102006 A1* | 4/2013 | Takeuchi | ........ | G01N 33/57484 435/6.12 |
| 2013/0137111 A1* | 5/2013 | Shindo | ........ | C12Q 1/6886 435/6.12 |
| 2014/0288116 A1* | 9/2014 | Bandla | ........ | A61P 35/00 514/300 |
| 2015/0315657 A1 | 11/2015 | Rhodes et al. | | |
| 2016/0304937 A1 | 10/2016 | Begovich et al. | | |

FOREIGN PATENT DOCUMENTS

| | | |
|---|---|---|
| CN | 104818320 | 8/2015 |
| EP | 2586862 A1 | 5/2013 |
| JP | 2016515380 A | 5/2016 |
| WO | 2011162295 A1 | 12/2011 |
| WO | 2014150300 A2 | 9/2014 |
| WO | WO2014144121 A2 | 9/2014 |
| WO | 2015148494 A1 | 10/2015 |
| WO | 2015164869 A1 | 10/2015 |
| WO | 2015149034 A9 | 12/2015 |
| WO | WO2016166269 A1 | 10/2016 |

OTHER PUBLICATIONS

International Search Report and Written Opinion dated Aug. 29, 2018 in corresponding PCT/EP2018/064172 filed on May 30, 2018, pp. 1-15.
Maruja E.L. et al., A Single-Tube Multiplexed Assay for Detecting ALK, ROS1, and RET Fusions in Lung Cancer, The Journal of Molecular Diagnostics, Mar. 1, 2014, pp. 229-243, vol. 16, No. 2, Elsevier Inc.
Okamoto, I., et al., Multiplex genomic profiling of non-small cell lung cancers from the LETS phase III trial of first-line S-1/carboplatin versus paclitaxel/carboplatin: results of a West Japan Oncology Group study, Oncotarget, Apr. 30, 2014, pp. 2293-2304, vol. 5, No. 8.
Rogers, T.-M., et al., Multiplexed transcriptome analysis to detect ALK, ROS1 and RET rearrangements in lung cancer, Scientific Reports, Feb. 9, 2017, Article No. 42259, pp. 1-8, vol. 7, No. 1.
AmoyDx EML4-ALK Fusion Gene Detection Kit—For qualitative detection of 21 EML4-ALK fusions—Instruction for Use, Jul. 2014.
AmoyDx RET Gene Fusions Detection Kit—For qualitative detection of 9 RET gene fusions—Instruction for Use, Jul. 2015.
Khoo, C., et al., Molecular methods for somatic mutation testing in lung adenocarcinoma: EGFR and beyond, Transl Lung Cancer Res, 2015, pp. 126-141, vol. 4, No. 2.
Kohno, T., et al., Beyond ALK-RET, ROS1 and other oncogene fusions in lung cancer, Transl Lung Cancer Res, 2015, pp. 156-164, vol. 4, No. 2.
Notice of Opposition filed by a strawman dated Mar. 22, 2022 in Application No. 18730279.9, 51 pages.
Observations filed by third party on Apr. 7, 2021 regarding European Patent Application published as EP3631011, 16 pages.

* cited by examiner (Continued)

Primary Examiner — Katherine D Salmon
(74) Attorney, Agent, or Firm — David J. Chang; Jennifer K. Rosenfield; Carol Johns

(57) ABSTRACT

Provided herein are methods and compositions for multiplex detection of a large number of actionable gene fusions with very high sensitivity and specificity. The present methods and compositions can detect ALK, RET, and ROS1 gene fusions, optionally in combination with other mutations and fusions.

25 Claims, 11 Drawing Sheets

Specification includes a Sequence Listing.

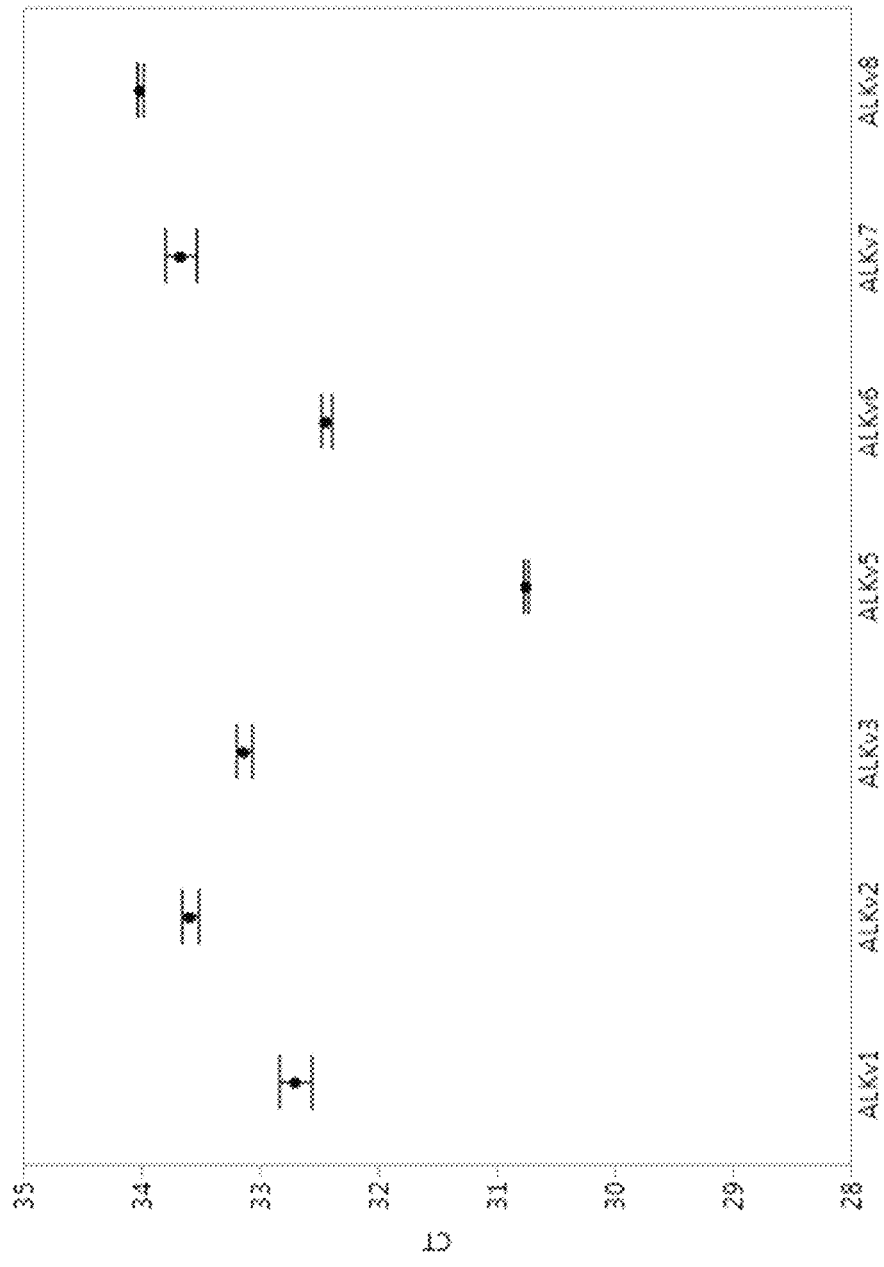

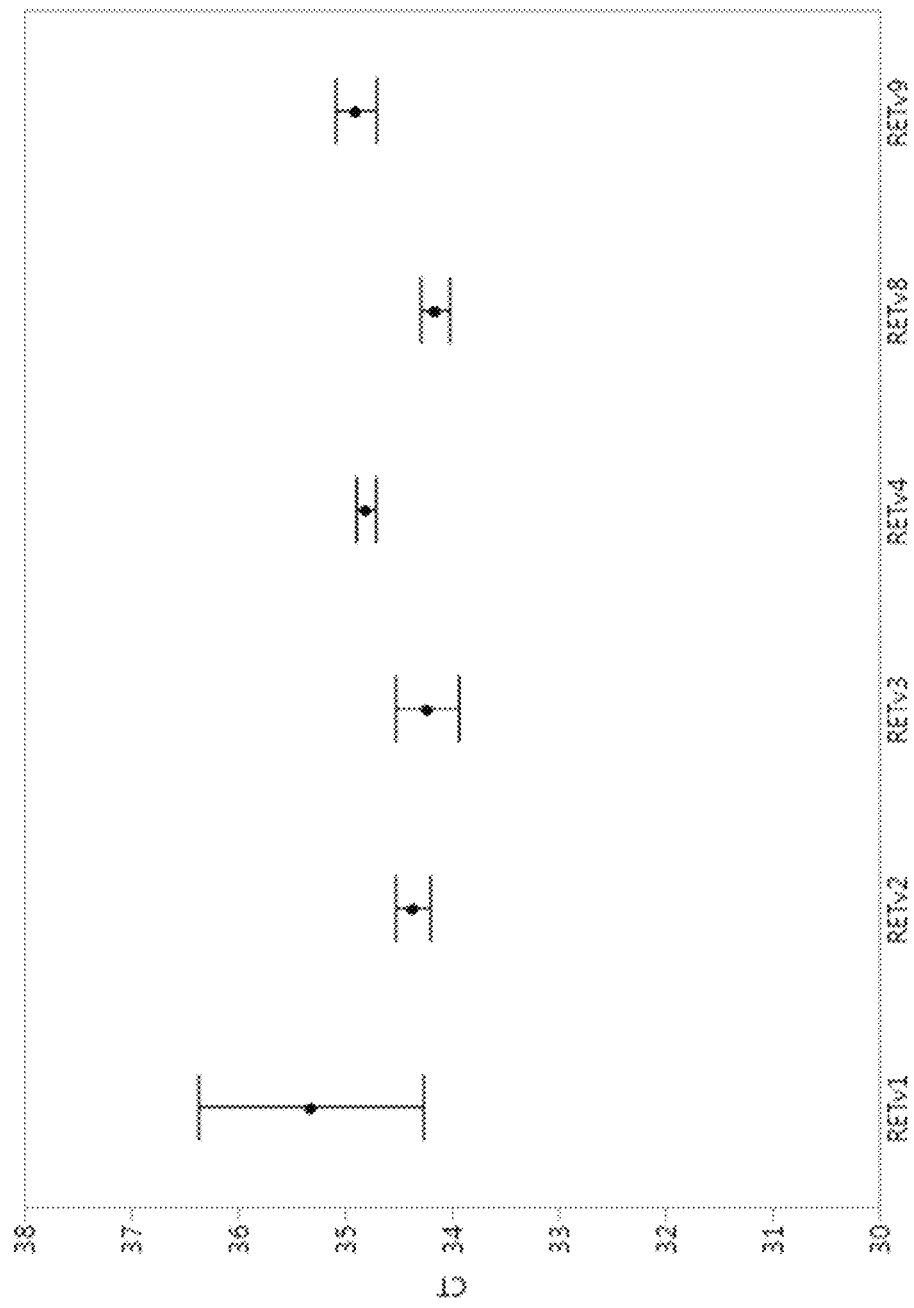

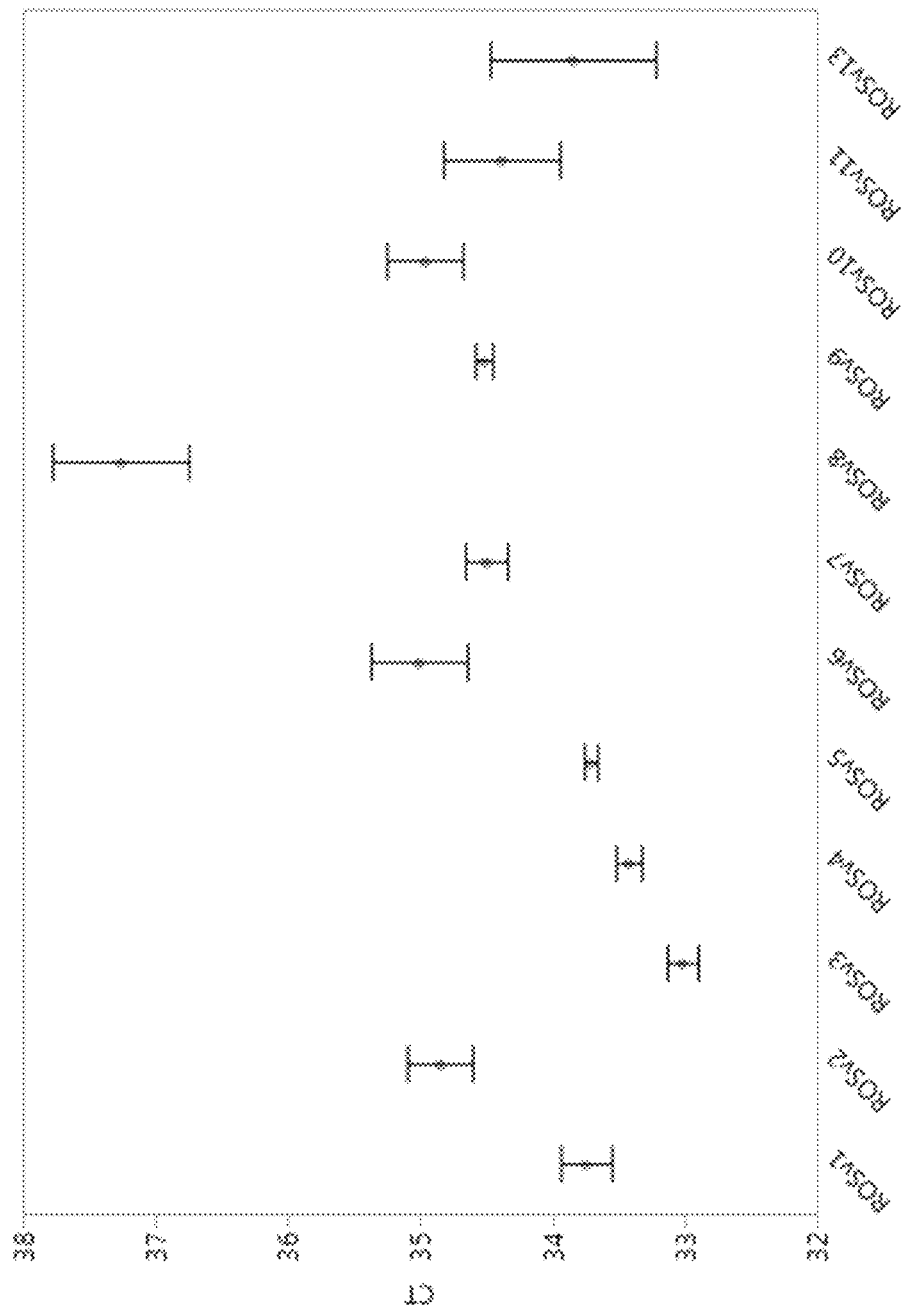

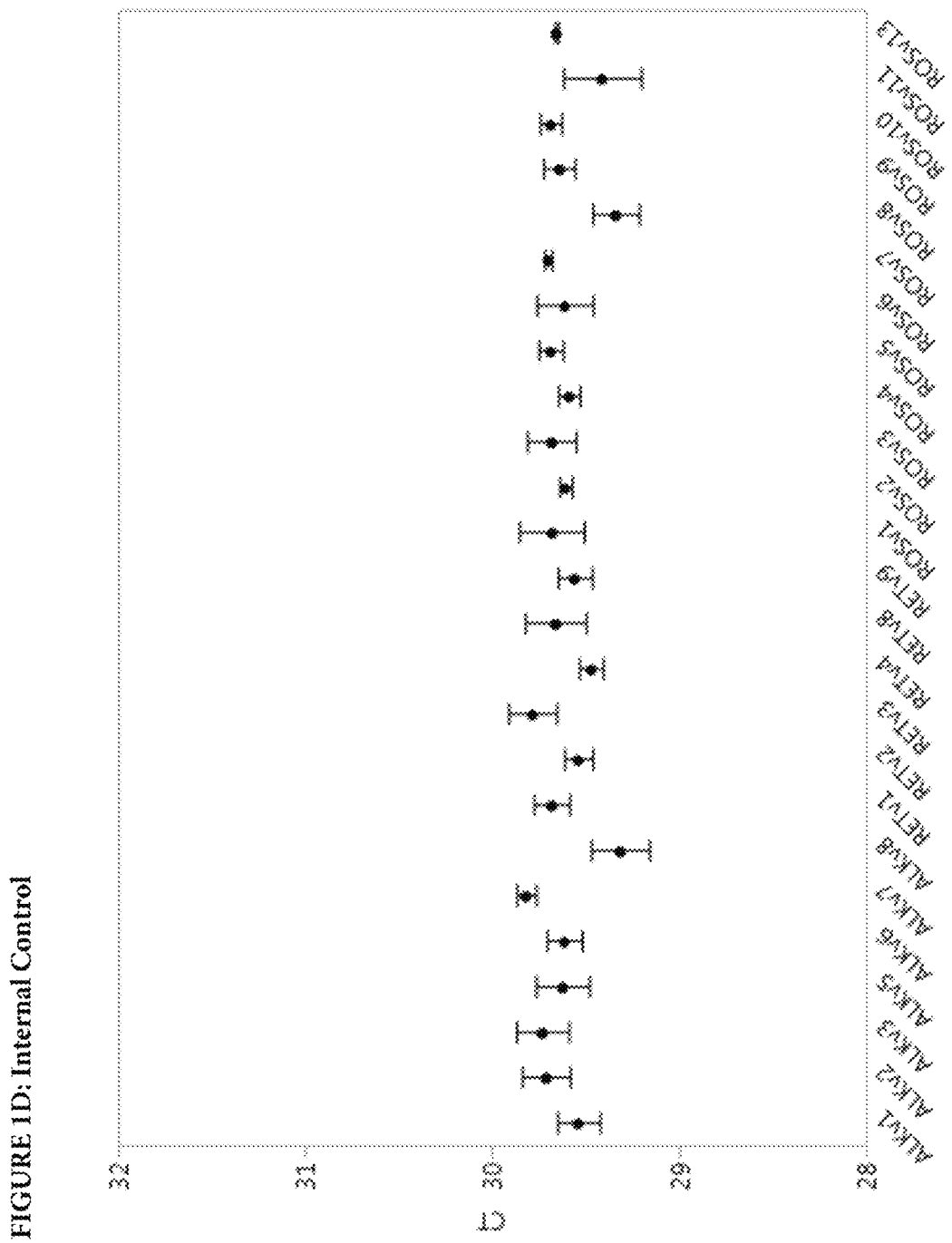
FIGURE 1D: Internal Control

```
                        SEQUENCE LISTING

<160> NUMBER OF SEQ ID NOS: 230

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acacctggga aaggacctaa a                                                 21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacacctggg aaaggaccta aa                                                22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccacacctgg gaaaggacct a                                                 21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```
ccacacctgg gaaaggacct                                              20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccacacctgg gaaaggacc                                               19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccacacctgg gaaaggac                                                18

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccacacctg ggaaaggac                                               19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcccacacct gggaaagga                                               19

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agcccacacc tgggaaag                                                18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagcccacac ctgggaaa                                                18

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgggagac tatgaaatat tgtact                                          26

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcgggagact atgaaatatt gtact                                           25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgggagacta tgaaatattg tact                                            24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcgggagac tatgaaatat tgtac                                           25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actcgggaga ctatgaaata ttgta                                           25

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aactcgggag actatgaaat attgta                                          26

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
taactcggga gactatgaaa tattgta                                              27

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
taactcggga gactatgaaa tattgt                                               26

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
taactcggga gactatgaaa tattgta                                              27

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
actcgggaga ctatgaaata ttgtac                                               26

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
aagcataaag atgtcatcat caaccaa                                              27

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
agcataaaga tgtcatcatc aaccaa                                               26

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gcataaagat gtcatcatca accaa                                          25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
cataaagatg tcatcatcaa ccaag                                          25

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gcataaagat gtcatcatca accaag                                         26

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gcataaagat gtcatcatca acca                                           24

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
gcataaagat gtcatcatca acc                                            23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
agcataaaga tgtcatcatc aacc                                           24

<210> SEQ ID NO 29

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagcataaag atgtcatcat caacc                                       25

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aagcataaag atgtcatcat caac                                        24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcagtgaaa aaatcagtct caag                                        24

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctcagtgaaa aaatcagtct caagt                                       25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcagtgaaaa aatcagtctc aagta                                       25

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcagtgaaaa aatcagtctc aagtaa                                      26

<210> SEQ ID NO 35
<211> LENGTH: 27
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cagtgaaaaa atcagtctca agtaaag                                27

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cagctctctg tgatgcgcta                                        20

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctctctgtga tgcgctact                                         19

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctctgtgat gcgctactca a                                      21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gctctctgtg atgcgctac                                         19

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctgtgatgcg ctactcaata g                                      21

<210> SEQ ID NO 41
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 41
agaagagggc attctgcaca                                                   20

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagggcattc tgcacaga                                                     18

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gagggcattc tgcacagat                                                    19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gaagagggca ttctgcacag                                                   20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gggcattctg cacagattg                                                    19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gaactagtcc agcttcgagc a                                                 21

<210> SEQ ID NO 47
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 47
tgaagaacta gtccagcttc ga                                                22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctagtccagc ttcgagcaca a                                                 21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aagaactagt ccagcttcga g                                                 21

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtccagcttc gagcacaag                                                    19

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
tctggcatag aagattaaag aatcaaaaaa gtgccaag                               38

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctctgcagc tccatctg                                                     18

<210> SEQ ID NO 53
<211> LENGTH: 18
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 53
ggctctgcag ctccatct                                                18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gggctctgca gctccatc                                                18

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gggctctgca gctccat                                                 17

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gggctctgca gctcca                                                  16

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgcagctcca tctgcatgg                                               19

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcagctccat ctgcatgg                                                18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
cagctccatc tgcatggc                                                   18

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
agctccatct gcatggc                                                    17

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gctccatctg catggct                                                    17

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gaattgctgt gggaaataat gatg                                           24

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaattgctgt gggaaataat gat                                            23

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
attgctgtgg gaaataatga tgtaaag                                        27

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttgctgtggg aaataatgat gtaaag                                         26

<210> SEQ ID NO 87
<211> LENGTH: 25
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 87
tgctgtggga ataatgatg taaag                                        25

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gctgtgggaa ataatgatgt aaag                                        24

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaattgctgt gggaaataat gatgtaaa                                    28

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gaattgctgt gggaaataat gatgtaa                                     27

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aattgctgtg ggaaataatg atgtaaa                                     27

<210> SEQ ID NO 92
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
attgctgtgg gaaataatga tgtaaa                                      26

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
attgctgtgg gaaataatga tgtaa                                          25

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aattgctgtg ggaaataatg atgta                                          25

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
attgctgtgg gaaataatga tgta                                           24

<210> SEQ ID NO 96
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gaattgctgt gggaaataat gatgta                                         26

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gaattgctgt gggaaataat gatgt                                          25

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
catgtcagct tcgtatctct caa                                            23

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
atgtcagctt cgtatctctc aa                                              22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
catgtcagct tcgtatctct ca                                              22

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gcatgtcagc ttcgtatctc tc                                              22

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
catgtcagct tcgtatctct c                                               21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gcatgtcagc ttcgtatctc t                                               21

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcatgtcagc ttcgtatctc                                                 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cagcatgtca gcttcgtatc                                           20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tagcagcatg tcagcttcgt a                                         21

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
agcagcatgt cagcttcg                                             18

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
aggacctggc tacaagagtt aa                                        22

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ggacctggct acaagagtta a                                         21

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ggacctggct acaagagtta aa                                        22

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aggacctggc tacaagagtt aaa                                        23

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
aggacctggc tacaagagtt a                                          21

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggacctggct acaagagtta                                            20

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gacctggcta caagagttaa aaag                                       24

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
acctggctac aagagttaaa aag                                        23

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
aggacctggc tacaagagtt                                            20

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117

```
ggacctggct acaagagtt                                                    19
```

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118

```
ttgaacagct cactaaagtg cacaaa                                            26
```

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119

```
tgaacagctc actaaagtgc acaaa                                             25
```

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

```
gaacagctca ctaaagtgca caa                                               24
```

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121

```
aacagctcac taaagtgcac aaa                                               23
```

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

```
acagctcact aaagtgcaca aa                                                22
```

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123

```
gaacagctca ctaaagtgca caa                                               23
```

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
aacagctcac taaagtgcac aa                                              22

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
acagctcact aaagtgcaca a                                               21

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gaacagctca ctaaagtgca ca                                              22

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aacagctcac taaagtgcac a                                               21

<210> SEQ ID NO 128
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tgcgcaaagc cagcgt                                                     16

<210> SEQ ID NO 129
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cgacctgcgc aaagcca                                                    17

<210> SEQ ID NO 130
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gacctgcgca aagccag                                              17

<210> SEQ ID NO 131
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
cctgcgcaaa gccagc                                               16

<210> SEQ ID NO 132
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acctgcgcaa agccagc                                              17

<210> SEQ ID NO 133
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ctgcgcaaag ccagcgt                                              17

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gacctgcgca aagccagc                                             18

<210> SEQ ID NO 135
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cgacctgcgc aaagcc                                               16

```
<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tgtatctcca tgccagagca g                                              21

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gtatctccat gccagagcag                                                20

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ctgtatctcc atgccagagc a                                              21

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gctgtatctc catgccagag                                                20

<210> SEQ ID NO 140
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ggctgtatct ccatgccaga ggctgtatct ccatgccaga                          40

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ggctgtatct ccatgccag                                                 19

<210> SEQ ID NO 142
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
aggctgtatc tccatgcca                                               19

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gaggctgtat ctccatgcca                                              20

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
agaggctgta tctccatgc                                               19

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gagaggctgt atctccatgc                                              20

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000
```

```
<210> SEQ ID NO 150
<400> SEQUENCE: 150
000

<210> SEQ ID NO 151
<400> SEQUENCE: 151
000

<210> SEQ ID NO 152
<400> SEQUENCE: 152
000

<210> SEQ ID NO 153
<400> SEQUENCE: 153
000

<210> SEQ ID NO 154
<400> SEQUENCE: 154
000

<210> SEQ ID NO 155
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160
<400> SEQUENCE: 160
000

<210> SEQ ID NO 161
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
agagtttttc caagaaccaa gttct                                           25

<210> SEQ ID NO 162
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
ctagagtttt tccaagaacc aagttct                                         27

<210> SEQ ID NO 163
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ctagagtttt tccaagaacc aagttc                                          26

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ctagagtttt tccaagaacc aagtt                                           25

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ctagagtttt tccaagaacc aagt                                            24

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ctagagtttt tccaagaacc aag                                             23

<210> SEQ ID NO 167
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 167
tagagttttt ccaagaacca agttctt                                           27

<210> SEQ ID NO 168
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gagtttttcc aagaaccaag ttctt                                             25

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
agttttccca agaaccaagt tctt                                              24

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170 gttttccaa gaaccaagtt ctt                                                23

<210> SEQ ID NO 171
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tagagttttt ccaagaacca agttct                                            26

<210> SEQ ID NO 172
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tagagttttt ccaagaacca agttc                                             25

<210> SEQ ID NO 173
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 173
agagtttttc caagaaccaa gttc                                            24

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
agagtttttc caagaaccaa gtt                                             23

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
agagtttttc caagaaccaa gt                                              22

<210> SEQ ID NO 176
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
ctcctagagt ttttccaaga accaa                                           25

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctcctagagt ttttccaaga acca                                            24

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tcctagagtt tttccaagaa ccaa                                            24

<210> SEQ ID NO 179
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 179
cctagagttt ttccaagaac caa                                              23

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gagtttttcc aagaaccaag ttct                                             24

<210> SEQ ID NO 181
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
tgcagctcca tctgcatggc ttgcagctcc atctgcatgg ct                         42

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
ccgccggaag caccaggagc                                                  20

<210> SEQ ID NO 183
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
taccgccgga agcaccagga gctgca                                           26

<210> SEQ ID NO 184
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
taccgccgga agcaccagga gctgc                                            25

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 185
taccgccgga agcaccagga gctg                                              24

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
taccgccgga agcaccagga gct                                               23

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ttgaacagct cactaaagtg ca                                                22

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
caaagccagc gtgacca                                                      17

<210> SEQ ID NO 189
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
atccaaagtg ggaattccct cggaagaac                                         29

<210> SEQ ID NO 190
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
ccaaagtggg aattccctcg gaagaac                                           27

<210> SEQ ID NO 191
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 191
tccaaagtgg gaattccctc ggaagaa                                          27

<210> SEQ ID NO 192
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
ccaaagtggg aattccctcg gaagaactt                                        29

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
tccaaagtgg gaattccctc ggaagaactt                                       30

<210> SEQ ID NO 194
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
atccaaagtg ggaattccct cggaagaact t                                     31

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cactgacgct ccaccgaa                                                    18

<210> SEQ ID NO 196
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
aagcccactg acgctcca                                                    18

<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 197
actgacgctc caccgaaa                                                    18

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gagctgtctg gctctgga                                                    18

<210> SEQ ID NO 199
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tgtctggctc tggagatctt gtctggctct ggagatct                              38

<210> SEQ ID NO 200
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ttgagagaac ggaggtcct                                                   19

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tgagagaacg gaggtcct                                                    18

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ttgagagaac ggaggtcctg                                                  20

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
```
ataaccatta gcagagaggc t                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aaccattagc agagaggctc a                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ataaccatta gcagagaggc t                                              21

<210> SEQ ID NO 206
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
agtagcgcct tccagct                                                   17

<210> SEQ ID NO 207
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
gccttccagc tggttgga                                                  18

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
gaagacaaag aaggcagaga ga                                             22

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ttcttaccac aacatgacag tagt                                          24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
tcttaccaca acatgacagt agtg                                          24

<210> SEQ ID NO 211
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
gaaaagacaa ttgatgacct ggagaaaaga caattgatga cctgga                  46

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
aagctggaaa agacaattga tgac                                          24

<210> SEQ ID NO 213
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
gtattgaatt tttactccct tctagtaatt tg                                 32

<210> SEQ ID NO 214
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gtattgaatt tttactccct tctagtaatt t                                  31

<210> SEQ ID NO 215
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
gtattgaatt tttactccct tctagtaatt                                    30

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tataagcact gtcacccctt                                              20

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
ataagcactg tcaccccctt                                              19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
tataagcact gtcacccct                                               19

<210> SEQ ID NO 219
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
ctttgtcttc gtttataagc actgtca                                      27

<210> SEQ ID NO 220
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
aactctttgt cttcgtttat aagcactgt                                    29

<210> SEQ ID NO 221
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
agccaactct tgtcttcgt ttataagca                                     29

```
<210> SEQ ID NO 222
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
cagtgggatt gtaacaacca gaaat                                           25

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gtcagtggga ttgtaacaac caga                                            24

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
gtcagtggga ttgtaacaac ca                                              22

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
cagtgggatt gtaacaacca gaaa                                            24

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
cagtgggatt gtaacaacca gaa                                             23

<210> SEQ ID NO 227
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
tggagtccca aataaaccag gcattccca                                       29
```

```
<210> SEQ ID NO 228
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
tgatttttgg ataccagaaa caagtttcat ac                                32

<210> SEQ ID NO 229
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
tggagtccca aataaaccag gcattccca                                    29

<210> SEQ ID NO 230
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
tgatttttgg ataccagaaa caagtttcat ac                                32
```

MULTIPLEX PCR DETECTION OF ALK, RET, AND ROS FUSIONS

CROSS-REFERENCE TO RELATED APPLICATIONS

The present application claims priority to U.S. Provisional Application No. 62/513,226, filed May 31, 2017, the disclosure of which is incorporated by reference herein.

SEQUENCE LISTING

The instant application contains a Sequence Listing which has been filed electronically in ASCII format and is hereby incorporated by reference in its entirety. Said ASCII copy, created on Jul. 11, 2018, is named 34290-US1_SL.txt and is 45,482 bytes in size.

BACKGROUND OF THE INVENTION

A number of cancers are associated with gene fusions (Yoshihara et al. (2015) *Oncogene* 34:4845). Perhaps the earliest reported example is the association of BCR-ABL with chronic myelogenous leukemia (CML) in the '60s (Nowell and Hungerford (1960) *J. Natl. Cancer Inst.* 25:85). Since then, hundreds more gene fusions have been reported for cancers in many different tissues (Presner and Chinnaiyan (2009) *Curr. Opin Genet. Dev.* 19:82).

Another example is the tyrosine receptor kinase ALK (anaplastic lymphoma kinase). EML4-ALK (echinoderm microtubule-associated protein-like 4-anaplastic lymphoma kinase) fusions are associated with non-small cell lung cancer (NSCLC). In this case, the N terminal, extracellular portion of ALK is replaced by EML4 (KIF5B, HIP1, KLC1, TFG can also fuse with ALK in a similar manner). The expression of the resulting fusion gene is driven by the strong EML4 promoter, resulting in higher expression of the intracellular tyrosine kinase domain of ALK. In addition, EML4 forms a coiled-coil that results in ligand-independent dimerization, and constitutive activation of the ALK tyrosine kinase domain. Additional examples of activated kinase fusions involve RET (rearranged during transfection) and ROS1.

Detection of a gene fusion can be used to direct therapy. Most methods of detection require biopsy of tumor tissue, which is not feasible for many cancer patients, especially in later stages. Detection in biopsied tissue sections is typically carried out by fluorescence in situ hybridization (FISH) or immunohistochemistry (IHC). The tests have high false positive rates and background, in part because of shearing during the sectioning process. Skilled cytologists are thus required to observe multiple tissue sections, which necessitates a sizable biopsy from a weakened patient. Similarly, a difficulty with using RT-PCR is the amount and quality of genetic material from tumor tissue, e.g., in formalin fixed paraffin embedded (FFPE) form. See, e.g., Liu et al. (2015) PLoSOne 10: e0117032.

Because detection is time and resource intensive, the testing rate is relatively low. Cancers associated with ALK fusions are very sensitive to ALK inhibitors such as crizotinib and ceretinib. Gene fusions with Rearranged during Transcription (RET), such as with KIF5B or CCDC6, are also sensitive to therapy, e.g., with vandetanib (see Matsubara et al. (2007) *J. Thorac. Oncol.* 7:1872). The low rate of testing for gene fusions thus represents a great lost opportunity for treatment.

SUMMARY OF THE INVENTION

Provided herein are multiplex methods and compositions for detecting fusion genes, in particular those involving ALK, RET, and ROS1.

Provided herein are multiplex assay compositions comprising: (A) at least one primer set and labeled probe that specifically amplify and detect at least one ALK fusion gene; (B) at least one primer set and labeled probe that specifically amplify and detect at least one RET fusion gene; (C) at least one primer set and labeled probe that specifically amplify and detect at least one ROS1 fusion gene; and (D) a primer set and labeled probe that specifically amplify and detect an internal control. Further provided are multiplex assay compositions comprising: (A) at least one primer set and labeled probe that specifically amplify and detect at least one ALK fusion gene; (B) at least one primer set and labeled probe that specifically amplify and detect at least one RET fusion gene; and (C) a primer set and labeled probe that specifically amplify and detect an internal control. Provided herein are multiplex assay compositions comprising: (A) at least one primer set and labeled probe that specifically amplify and detect at least one RET fusion gene; and (B) a primer set and labeled probe that specifically amplify and detect an internal control.

In some embodiments, the at least one ALK fusion gene is selected from the group consisting of: EML4 exon 13-ALK exon 20, EML4 exon 20-ALK exon 20, EML4 exon 6a/b-ALK exon 20, EML4 exon 2-ALK exon 20, EML4 exon 18-ALK exon 20, KIF5B exon 17-ALK exon 20, and KIF5B exon 24-ALK exon 20; the at least one RET fusion gene is selected from the group consisting of: KIF5B exon 15-RET exon 12, KIF5B exon 16-RET exon 12, KIF5B exon 22-RET exon 12, KIF5B exon 23-RET exon 12, CCDC6 exon 1-RET exon 12, and NCOA4 exon 6-RET exon 12; and the at least one ROS1 fusion gene is selected from the group consisting of: CD74 exon 6-ROS1 exon 34, CD74 exon 6-ROS1 exon 32, EZR exon 10-ROS1 exon 34, TPM3 exon 8-ROS1 exon 35, SDC4 exon 4-ROS1 exon 32, SDC4 exon 2-ROS1 exon 32, SDC4 exon 2-ROS1 exon 34, SDC4 exon 4-ROS1 exon 34, SLC34A2 exon 13-ROS1 exon 34, SLC34A2 exon 13-ROS1 exon 32, SLC34A2 exon 4-ROS1 exon 32, SLC34A2 exon 4-ROS1 exon 35, and LRIG3 exon 16-ROS1 exon 35, in any combination.

In some embodiments, the composition comprises at least one primer set and probe that amplify and detect more than 2 ALK fusion genes, more than 2 RET fusion genes, and/or more than 2 ROS1 fusion genes. In some embodiments, the composition comprises at least one primer set and probe that amplify and detect EML4 exon 13-ALK exon 20, EML4 exon 20-ALK exon 20, EML4 exon 6a/b-ALK exon 20, KIF5B exon 15-RET exon 12, KIF5B exon 16-RET exon 12, KIF5B exon 22-RET exon 12, CD74 exon 6-ROS1 exon 34, and EZR exon 10-ROS1 exon 34.

In some embodiments, the at least one ALK fusion gene include: EML4 exon 13-ALK exon 20, EML4 exon 20-ALK exon 20, EML4 exon 6a/b-ALK exon 20, EML4 exon 2-ALK exon 20, EML4 exon 18-ALK exon 20, KIF5B exon 17-ALK exon 20, and KIF5B exon 24-ALK exon 20; the at least one RET fusion gene includes: KIF5B exon 15-RET exon 12, KIF5B exon 16-RET exon 12, KIF5B exon 22-RET exon 12, KIF5B exon 23-RET exon 12, CCDC6 exon 1-RET exon 12, and NCOA4 exon 6-RET exon 12; and the at least one ROS1 fusion gene includes: CD74 exon 6-ROS1 exon 34, CD74 exon 6-ROS1 exon 32, EZR exon 10-ROS1 exon 34, TPM3 exon 8-ROS1 exon 35, SDC4 exon 4-ROS1 exon 32, SDC4 exon 2-ROS1 exon 34, SDC4 exon 2-ROS1 exon 32, SDC4 exon 4-ROS1 exon 32, SLC34A2 exon 13-ROS1 exon 34, SLC34A2 exon 13-ROS1 exon 32, SLC34A2 exon 4-ROS1 exon 32, SLC34A2 exon 4-ROS1 exon 35, and LRIG3 exon 16-ROS1 exon 35. That is, the assay composition includes primer sets and probes to amplify and detect all of the listed fusion genes.

In some embodiments, for the primer set to amplify at least one ALK fusion gene, the forward primer and reverse primer have sequences selected from the group consisting of SEQ ID NOs:1-50, and SEQ ID NOs:52-61 and 181, respectively. In some embodiments, for the probe to detect at least one ALK fusion gene, the probe sequence is selected from the group consisting of SEQ ID NOs:182-186. The forward and reverse primer sequences and probe sequences can be used together in any appropriate combination to detect any 1, 2, 3, 4, 5, 6, or 7 ALK fusion variants in any combination. In some embodiments, for the primer set to amplify at least one RET fusion gene, the forward primer and reverse primer have sequences selected from the group consisting of SEQ ID NOs:83-145 and 187, and SEQ ID NOs:161-180, respectively. In some embodiments, for the probe to detect at least one RET fusion gene, the probe sequence is selected from the group consisting of: 189-194. The forward and reverse primer sequences and probe sequences can be used together in any combination to detect any 1, 2, 3, 4, 5, or 6 RET fusion variants in any combination. In some embodiments, for the primer set to detect at least one ROS1 fusion gene, the forward primer and reverse primer have sequences selected from the group consisting of SEQ ID NOs:195-212, and SEQ ID NOs:213-226, respectively. In some embodiments, for the probe to detect at least one ROS1 fusion gene, the probe sequence is selected from the group consisting of: 227-230 and 51. The forward and reverse primer sequences and probe sequences can be used together in any combination to detect any 1, 2, 3, 4, 5, 6, 7, 8, 9, 10, 11, 12, or 13 ROS1 fusion variants in any combination.

In some embodiments, the label on labeled probe that detects the internal control is different from the labels on the labeled probes that detect the fusion genes. In some embodiments, the labels on all of the labeled probes are different from each other. In some embodiments, a single labeled probe is used to detect all of the at least one ALK fusion genes. In some embodiments, a single labeled probe is used to detect all of the at least one RET fusion genes. In some embodiments, a single labeled probe is used to detect all of the at least one ROS1 fusion genes. In some embodiments, the labeled probe is attached to a primer in the at least one primer set. In some embodiments, the labeled probe is separate from the primer set.

In some embodiments, where more than one ALK fusion gene is amplified and detected, all of the primer sets that amplify the ALK fusion genes include a single common primer. In some embodiments, where more than one ALK fusion gene is amplified and detected, the primer sets include unique primers. In some embodiments, where more than one RET fusion gene is amplified and detected, all of the primer sets that amplify the RET fusion genes include a single common primer. In some embodiments, where more than one RET fusion gene is amplified and detected, the primer sets include unique primers. In some embodiments, where more than one ROS1 fusion gene is amplified and detected, all of the primer sets that amplify the ROS1 fusion genes include a single common primer. In some embodiments, where more than one ROS1 fusion gene is amplified and detected, the primer sets include unique primers.

Further provided herein are multiplex assay compositions comprising: (A) at least one primer set and labeled probe that specifically amplify and detect at least one ALK fusion gene; (B) at least one primer set and labeled probe that specifically amplify and detect at least one RET fusion gene; and (C) a primer set and labeled probe that specifically amplify and detect an internal control. Also provided herein are multiplex assay compositions comprising: (A) at least one primer set and labeled probe that specifically amplify and detect at least one RET fusion gene; and (B) a primer set and labeled probe that specifically amplify and detect an internal control. In some embodiments, at least one ROS1 fusion gene is amplified and detected in a separate multiplex assay. In some embodiments, the at least one ALK fusion gene is selected from the group consisting of: EML4 exon 13-ALK exon 20, EML4 exon 20-ALK exon 20, EML4 exon 6a/b-ALK exon 20, EML4 exon 2-ALK exon 20, EML4 exon 18-ALK exon 20, KIF5B exon 17-ALK exon 20, and KIF5B exon 24-ALK exon 20; and the at least one RET fusion gene is selected from the group consisting of: KIF5B exon 15-RET exon 12, KIF5B exon 16-RET exon 12, KIF5B exon 22-RET exon 12, KIF5B exon 23-RET exon 12, CCDC6 exon 1-RET exon 12, and NCOA4 exon 6-RET exon 12, in any combination. In some embodiments, the at least one ROS1 fusion gene is selected from the group consisting of: CD74 exon 6-ROS1 exon 34, CD74 exon 6-ROS1 exon 32, EZR exon 10-ROS1 exon 34, TPM3 exon 8-ROS1 exon 35, SDC4 exon 2-ROS1 exon 34, SDC4 exon 4-ROS1 exon 32, SDC4 exon 2-ROS1 exon 32, SDC4 exon 4-ROS1 exon 34, SLC34A2 exon 13-ROS1 exon 34, SLC34A2 exon 13-ROS1 exon 32, SLC34A2 exon 4-ROS1 exon 32, SLC34A2 exon 4-ROS1 exon 35, and LRIG3 exon 16-ROS1 exon 35.

In some embodiments, the composition comprises at least one primer set and probe that amplify and detect more than 2 ALK fusion genes and more than 2 RET fusion genes. In some embodiments, the composition comprises at least one primer set and probe that amplify and detect EML4 exon 13-ALK exon 20, EML4 exon 20-ALK exon 20, EML4 exon 6a/b-ALK exon 20, KIF5B exon 15-RET exon 12, KIF5B exon 16-RET exon 12, and KIF5B exon 22-RET exon 12.

In some embodiments, the at least one ALK fusion gene include: EML4 exon 13-ALK exon 20, EML4 exon 20-ALK exon 20, EML4 exon 6a/b-ALK exon 20, EML4 exon 2-ALK exon 20, EML4 exon 18-ALK exon 20, KIF5B exon 17-ALK exon 20, and KIF5B exon 24-ALK exon 20; and the at least one RET fusion gene includes: KIF5B exon 15-RET exon 12, KIF5B exon 16-RET exon 12, KIF5B exon 22-RET exon 12, KIF5B exon 23-RET exon 12, CCDC6 exon 1-RET exon 12, and NCOA4 exon 6-RET exon 12.

In some embodiments, the label on labeled probe that detects the internal control is different from the labels on the labeled probes that detect the fusion genes. In some embodiments, the labels on all of the labeled probes are different from each other. In some embodiments, a single labeled probe is used to detect all of the at least one ALK fusion genes. In some embodiments, a single labeled probe is used to detect all of the at least one RET fusion genes. In some embodiments, the labeled probe is attached to a primer in the at least one primer set. In some embodiments, the labeled probe is separate from the primer set.

In some embodiments, where more than one ALK fusion gene is amplified and detected, all of the primer sets that amplify the ALK fusion genes include a single common primer. In some embodiments, where more than one ALK fusion gene is amplified and detected, the primer sets include unique primers. In some embodiments, where more than one RET fusion gene is amplified and detected, all of the primer sets that amplify the RET fusion genes include a single common primer. In some embodiments, where more than one RET fusion gene is amplified and detected, the primer sets include unique primers.

Examples of internal controls that can be used for the presently disclosed assays include, but are not limited to, SDHA (succinate dehydrogenase), LDHA (lactate dehydrogenase A), NONO, PGK (phosphoglycerate kinase 1), PPIH, HPRT1, beta-actin, GADPH, ACTB, and 16S rRNA.

In some embodiments, the composition further comprises a DNA polymerase, e.g., a thermostable DNA polymerase such as Taq or a Taq derivative. In some embodiments, the composition further comprises reverse transcriptase. In some embodiments, the composition further comprises dNTPs. In some embodiments, the composition further comprises buffer amenable to polymerization by the DNA polymerase and reverse transcriptase.

In some embodiments, the composition further comprises a biological sample from an individual or group of individuals. In some embodiments, the individual has been diagnosed with cancer, e.g., lung cancer (e.g., non-small cell lung cancer (NSCLC), lung squamous cell carcinoma, lung adenocarcinoma), bladder carcinoma, glioblastoma, head and neck cancer, glioma, thyroid carcinoma, ovarian cancer, leukemia, lymphoma, prostate cancer, pancreatic cancer, renal cancer, or breast cancer.

In some embodiments, the sample is enriched or isolated nucleic acid, e.g., DNA or RNA. In some embodiments, the sample is RNA, e.g., isolated from blood (e.g., serum, plasma, other blood fraction), bronchoalveolar lavage, or tissue biopsy. In some embodiments, the biological sample includes 100 nM or less of the polynucleotide comprising the fusion gene, e.g., 0.01-100 nM, 0.01-25 nM, 0.01-5 nM, 0.02-0.5 nM, or 0.02-0.1 nM.

Further provided are methods of identifying an individual with cancer comprising contacting a biological sample from the individual with any of the multiplex assay compositions described herein (e.g., comprising: (A) at least one primer set and labeled probe that specifically amplify and detect at least one ALK fusion gene; (B) at least one primer set and labeled probe that specifically amplify and detect at least one RET fusion gene; (C) at least one primer set and labeled probe that specifically amplify and detect at least one ROS1 fusion gene; and (D) a primer set and labeled probe that specifically amplify and detect an internal control); carrying out amplification and detection under conditions that allow formation and detection of an amplification product in the presence of at least one fusion gene in the biological sample; determining that at least one fusion gene is present if a fusion gene is detected in step B; whereby the presence of at least one fusion gene in said individual's sample indicates sensitivity of said individual to a kinase inhibitor therapy if at least one fusion gene is present.

Further provided are methods of determining the likelihood of response of an individual with cancer to kinase therapy comprising contacting a biological sample from the individual with any of the multiplex assay compositions described herein (e.g., comprising: (A) at least one primer set and labeled probe that specifically amplify and detect at least one ALK fusion gene; (B) at least one primer set and labeled probe that specifically amplify and detect at least one RET fusion gene; (C) at least one primer set and labeled probe that specifically amplify and detect at least one ROS1 fusion gene; and (D) a primer set and labeled probe that specifically amplify and detect an internal control); carrying out amplification and detection under conditions that allow formation and detection of an amplification product in the presence of at least one fusion gene in the biological sample; determining that at least one fusion gene is present if a fusion gene is detected in step B; and determining that the individual will likely respond to the kinase inhibitor therapy.

Further provided are methods of treating an individual, e.g., an individual diagnosed with cancer, comprising contacting a biological sample from the individual with any of the multiplex assay compositions described herein (e.g., comprising: (A) at least one primer set and labeled probe that specifically amplify and detect at least one ALK fusion gene; (B) at least one primer set and labeled probe that specifically amplify and detect at least one RET fusion gene; (C) at least one primer set and labeled probe that specifically amplify and detect at least one ROS1 fusion gene; and (D) a primer set and labeled probe that specifically amplify and detect an internal control); carrying out amplification and detection under conditions that allow formation and detection of an amplification product in the presence of at least one fusion gene in the biological sample; determining that at least one fusion gene is present if a fusion gene is detected; and treating the individual if at least one fusion gene is present. Further provided are methods of treating an individual, e.g., an individual diagnosed with cancer, comprising contacting a biological sample from the individual with any of the multiplex assay compositions described herein (e.g., comprising: (A) at least one primer set and labeled probe that specifically amplify and detect at least one ALK fusion gene; (B) at least one primer set and labeled probe that specifically amplify and detect at least one RET fusion gene; and (C) a primer set and labeled probe that specifically amplify and detect an internal control); carrying out amplification and detection under conditions that allow formation and detection of an amplification product in the presence of at least one fusion gene in the biological sample; determining that at least one fusion gene is present if a fusion gene is detected; and treating the individual if at least one fusion gene is present. Further provided are methods of treating an individual, e.g., an individual diagnosed with cancer, comprising contacting a biological sample from the individual with any of the multiplex assay compositions described herein (e.g., comprising: (A) at least one primer set and labeled probe that specifically amplify and detect at least one RET fusion gene; and (B) a primer set and labeled probe that specifically amplify and detect an internal control); carrying out amplification and detection under conditions that allow formation and detection of an amplification product in the presence of at least one fusion gene in the biological sample; determining that at least one fusion gene is present if a fusion gene is detected; and treating the individual if at least one fusion gene is present.

In some embodiments, the treatment is with a kinase inhibitor, e.g., a selective kinase inhibitor such as alectinib, crizotinib, ceritinib, lorlatinib, brigatinib, cabozantinib, apatinib, vandetanib, ponatinib, lenvatinib, DS6051b, or variants or combinations thereof. In some embodiments, the course of treatment includes radiation therapy or chemotherapy (e.g., cisplatin, carboplatin, paclitaxel, docetaxel). In some embodiments, the treatment is with GSK1838705A, TAE-684, CEP-14083, AP26113, NMS-E628, sorafenib, vandetanib, motesanib, sunitinib, and XL-184 (see, e.g., Mologni (2011) *Curr. Med. Chem.* 18:162).

In some embodiments, the individual is monitored throughout treatment, e.g., to determine if the amount of fusion gene amplification product increases or decreases, or if a different fusion gene is detected. In some embodiments, the treatment is changed if the amount of fusion gene amplification product changes, or if a different fusion gene is detected. For example, if the amount of the originally detected fusion gene decreases but the cancer is progressing, treatment can be changed to be less targeted, e.g., radio- or chemotherapy. If the individual's condition has improved, treatment can be reduced.

In some embodiments, the biological sample includes DNA or RNA, e.g., separated or purified nucleic acids. In some embodiments, the biological sample is RNA from blood, e.g., plasma, serum, or other blood fraction. In some embodiments, the amplification and detection are carried out using qRT-PCR.

In some embodiments, the individual is diagnosed with lung cancer (e.g., non-small cell lung cancer (NSCLC), lung squamous cell carcinoma, lung adenocarcinoma), bladder carcinoma, glioblastoma, head and neck cancer, glioma, thyroid carcinoma, ovarian cancer, leukemia, lymphoma, prostate cancer, pancreatic cancer, renal cancer, or breast cancer.

Further provided are methods for determining the presence of at least one fusion gene in a sample from an individual, e.g., an individual diagnosed with cancer, comprising contacting a biological sample from the individual with any of the multiplex assay compositions described herein (e.g., comprising: (A) at least one primer set and labeled probe that specifically amplify and detect at least one ALK fusion gene; (B) at least one primer set and labeled probe that specifically amplify and detect at least one RET fusion gene; (C) at least one primer set and labeled probe that specifically amplify and detect at least one ROS1 fusion gene; and (D) a primer set and labeled probe that specifically amplify and detect an internal control); carrying out amplification and detection under conditions that allow formation and detection of an amplification product in the presence of at least one fusion gene in the biological sample; determining that at least one fusion gene is present if a fusion gene is detected. Further provided are methods for determining the presence of at least one fusion gene in a sample from an individual, e.g., an individual diagnosed with cancer, comprising contacting a biological sample from the individual with any of the multiplex assay compositions described herein (e.g., comprising: (A) at least one primer set and labeled probe that specifically amplify and detect at least one ALK fusion gene; (B) at least one primer set and labeled probe that specifically amplify and detect at least one RET fusion gene; and (C) a primer set and labeled probe that specifically amplify and detect an internal control); carrying out amplification and detection under conditions that allow formation and detection of an amplification product in the presence of at least one fusion gene in the biological sample; determining that at least one fusion gene is present if a fusion gene is detected. Further provided are methods for determining the presence of at least one fusion gene in a sample from an individual, e.g., an individual diagnosed with cancer, comprising contacting a biological sample from the individual with any of the multiplex assay compositions described herein (e.g., comprising: (A) at least one primer set and labeled probe that specifically amplify and detect at least one RET fusion gene; and (B) a primer set and labeled probe that specifically amplify and detect an internal control); carrying out amplification and detection under conditions that allow formation and detection of an amplification product in the presence of at least one fusion gene in the biological sample; determining that at least one fusion gene is present if a fusion gene is detected.

In some embodiments, the biological sample includes DNA or RNA, e.g., separated or purified nucleic acids. In some embodiments, the biological sample is RNA from blood, e.g., plasma, serum, or other blood fraction. In some embodiments, the amplification and detection are carried out using qRT-PCR.

In some embodiments, the individual is diagnosed with lung cancer (e.g., non-small cell lung cancer (NSCLC), lung squamous cell carcinoma, lung adenocarcinoma), bladder carcinoma, glioblastoma, head and neck cancer, glioma, thyroid carcinoma, ovarian cancer, leukemia, lymphoma, prostate cancer, pancreatic cancer, renal cancer, or breast cancer.

In some embodiments, the method further comprises determining a course of treatment if at least one fusion gene is detected. In some embodiments, the treatment is with a kinase inhibitor, e.g., a selective kinase inhibitor such as alectinib, crizotinib, ceritinib, lorlatinib, brigatinib, cabozantinib, apatinib, vandetanib, ponatinib, lenvatinib, DS6051b, or variants or combinations thereof. In some embodiments, the course of treatment includes radiation therapy or chemotherapy (e.g., cisplatin, carboplatin, paclitaxel, docetaxel). In some embodiments, the treatment is with GSK1838705A, TAE-684, CEP-14083, AP26113, NMS-E628, sorafenib, vandetanib, motesanib, sunitinib, and XL-184.

BRIEF DESCRIPTION OF THE DRAWINGS

FIG. 1A shows that the indicated ALK fusion variants (FAM) are detectable at 50 copies in 0.1 ng WT RNA (n=3). FIG. 1B shows that the indicated RET fusion variants (HEX) are detectable at 50 copies in 0.1 ng WT RNA (n=3). FIG. 1C shows that the indicated ROS1 fusion variants (JA270) are detectable at 50 copies in 0.1 ng WT RNA (n=3). FIG. 1D shows the internal control Ct values for each input RNA.

DETAILED DESCRIPTION OF THE INVENTION

I. Introduction

Figure 2:
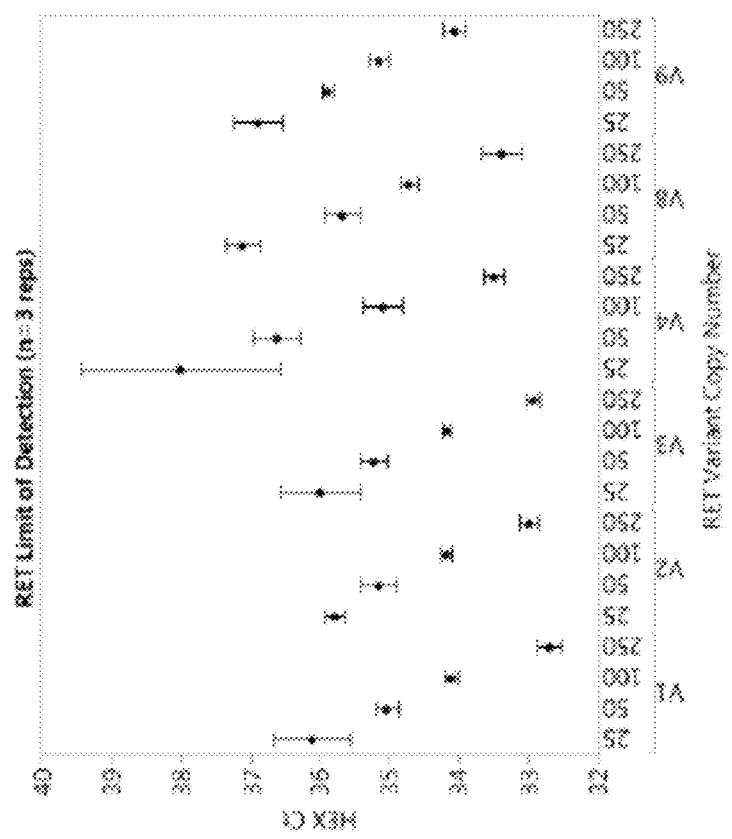
FIG. 2 shows the limit of detection of ALK and RET fusions in a multiplex assay as described herein. The assay is able to detect 25 copies of fusion transcript diluted in UHR.

The inventors have discovered a novel, quantitative, and multiplex method of detecting fusions between genetic regions. The presently disclosed methods require only a small amount of patient sample that can be gathered non-invasively, e.g., circulating free RNA (cfRNA) from plasma.

Current tests require either biopsy or large amounts of plasma, due to the limited amount of circulating nucleic acids originating from a tumor. The presently described methods allow for an extremely sensitive (down to ~25 copies), one-tube assay to detect multiple gene fusions that are predictive of cancer and response to therapy. The present assays can be used for identification of a fusion variant, as well as monitoring and surveillance during treatment and/or progression.

II. Definitions

A "genetic fusion" is hybrid chromosomal sequence formed by joining of two chromosomal locations that were previously separate. Fusion can occur between genes on the same chromosome (e.g., interstitial deletion or chromosomal inversion) or on different chromosomes (e.g., translocation).

A "fusion gene" is a hybrid gene formed by the joining of two genes that were previously separate, leading to a structural rearrangement and/or variant in the tumor genome. The fusion gene need not necessarily include coding sequence from both genes, but can include non-coding sequence from one of the genes, e.g., promoter or 3' untranslated regions. The denomination of genes that comprise a fusion gene as "gene 1," "gene 2," "gene A," "gene B," etc., is used to distinguish between genes that make up the fusion and does not necessarily refer to the position of the genes in the fusion. The terms ALK fusion, RET fusion, and ROS1 fusion refer to fusion genes that include ALK, RET, and ROS1 as a member, respectively.

The terms "fusion site," "fusion point," "breakpoint" and like terms refer to the point in a genetic fusion where a nucleotide from one gene or genetic location is found adjacent to a nucleotide from another gene or genetic location.

The terms "target region," "target portion," "target fragment," and like terms refer to a region of a target nucleic acid sequence that is to be amplified and/or analyzed.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The term "primer" refers to a short nucleic acid (an oligonucleotide) that acts as a point of initiation of polynucleotide strand synthesis by a nucleic acid polymerase under suitable conditions. Polynucleotide synthesis and amplification reactions typically include an appropriate buffer, dNTPs and/or rNTPs, and one or more optional cofactors, and are carried out at a suitable temperature. A primer typically includes at least one target-hybridized region that is at least substantially complementary to the target sequence. This region of is typically about 15 to about 40 nucleotides in length. A "primer pair" refers to a forward primer and reverse primer (sometimes called 5' and 3' primers) that are complementary to opposite strands of a target sequence and designed to amplify the target sequence. The forward and reverse primers are arranged within an amplifiable distance of each other on the target sequence, e.g., about 10-5000 nucleotides, about 25-500, or about 60-120 nucleotides. A "primer set" refers to one or more primer pairs, or a combination of at least one forward primer and at least one reverse primer. For example, a primer set can include 3 forward primers and 1 reverse primer, so that 3 distinct amplification products can potentially be produced.

A primer set or primer pair that is specific for a sequence (or portion of a gene) that is 5' (or 3') of a fusion site (or breakpoint) refers to primers used to amplify a sequence that does not include the fusion site or breakpoint.

As used herein, "probe" means any molecule that is capable of selectively binding to a specifically intended target biomolecule, for example, a nucleic acid sequence of interest to be bound, captured or hybridized by the probes. Probes are typically labeled with a non-naturally occurring moiety, e.g., a fluorophore, chromophore, affinity tag (e.g., streptavidin or biotin), and/or a quencher.

The words "complementary" or "complementarity" refer to the ability of a nucleic acid in a polynucleotide to form a base pair with another nucleic acid in a second polynucleotide. For example, the sequence A-G-T (A-G-U for RNA) is complementary to the sequence T-C-A (U-C-A for RNA). Complementarity may be partial, in which only some of the nucleic acids match according to base pairing, or complete, where all the nucleic acids match according to base pairing. A probe or primer is considered "specific for" a target sequence if it is at least partially complementary to the target sequence. Depending on the conditions, the degree of complementarity to the target sequence is typically higher for a shorter nucleic acid such as a primer (e.g., greater than 80%, 90%, 95%, or higher) than for a longer sequence.

The terms "identical" or "percent identity," in the context of two or more nucleic acids, or two or more polypeptides, refer to two or more sequences or subsequences that are the same or have a specified percentage of nucleotides, or amino acids, that are the same (e.g., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an a sequence that is at least about 8-25 amino acids or nucleotides in length, or over a region that is 50-100 amino acids or nucleotides in length, or over the entire length of the reference sequence.

The term "allele" refers to a sequence variant of a gene. One or more genetic differences can constitute an allele.

The term "kit" refers to any manufacture (e.g., a package or a container) including at least one reagent, such as a nucleic acid probe or probe pool or the like, for specifically amplifying, capturing, tagging/converting or detecting RNA or DNA as described herein.

The term "amplification conditions" refers to conditions in a nucleic acid amplification reaction (e.g., PCR amplification) that allow for hybridization and template-dependent extension of the primers. The terms "amplicon" and "amplification product" refer to a nucleic acid molecule that contains all or a fragment of the target nucleic acid sequence and that is formed as the product of in vitro amplification by any suitable amplification method. The borders of a given amplicon are typically defined by the position of the complementary portion of the forward and reverse primers used for amplification. Suitable PCR conditions are described in *PCR Strategies* (Innis et al., 1995, Academic Press, San Diego, Calif.) at Chapter 14; *PCR Protocols: A Guide to Methods and Applications* (Innis et al., Academic Press, N Y, 1990)

The term "thermostable nucleic acid polymerase" or "thermostable polymerase" refers to a polymerase enzyme, which is relatively stable at elevated temperatures when compared, for example, to polymerases from *E. coli*. A thermostable polymerase is suitable for use under temperature cycling conditions typical of the polymerase chain reaction ("PCR"). Exemplary thermostable polymerases include those from *Thermus thermophilus, Thermus caldophilus, Thermus* sp. Z05 (see, e.g., U.S. Pat. No. 5,674,738) and mutants of the *Thermus* sp. Z05 polymerase, *Thermus aquaticus, Thermus flavus, Thermus filiformis, Thermus* sp. sps17, *Deinococcus radiodurans*, Hot Spring family B/clone 7, *Bacillus stearothermophilus, Bacillus caldotenax, Thermotoga maritima, Thermotoga neapolitana* and *Thermosipho africanus*, and modified versions thereof.

The term "sample" or "biological sample" refers to any composition containing or presumed to contain nucleic acid from an individual. The term includes purified or separated components of cells, tissues, or blood, e.g., DNA, RNA, proteins, cell-free portions, or cell lysates. In some embodiments, analysis is conducted on plasma samples isolated from blood; the terms "detected in patient's blood" and "detected in patient's plasma" are used interchangeably to mean that blood is obtained from the patient and plasma derived therefrom is used for the analysis. A sample can also refer to other types of biological samples, e.g., skin, plasma, serum, whole blood and blood components (e.g., platelets, buffy coat), saliva, urine, tears, seminal fluid, vaginal fluids, tissue biopsies, and other fluids and tissues, including paraffin embedded tissues. Samples also may include constituents and components of in vitro cultures of cells obtained from an individual, including cell lines.

A "control" sample or value refers to a sample that serves as a reference, usually a known reference, for comparison to a test sample or test conditions. For example, a test sample can be taken from a test condition, e.g., from an individual suspected of having cancer, and compared to samples from known conditions, e.g., from a cancer-free individual (negative control), or from an individual known to have cancer and/or a particular genetic abnormality (positive control). In the context of the present disclosure, an example of a negative control would be a biological sample from a known healthy (non-cancer, non-mutated) individual, and an example of a positive control would be a biological sample from a patient or cell line known to have a particular gene fusion. A control can also represent an average value or a range gathered from a number of tests or results. A control can also be prepared for reaction conditions. For example, a positive control for the presence of nucleic acid could include primers or probes that will detect a sequence known to be present in the sample, while a negative control would be free of nucleic acids. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

An "internal control" (IC) refers to a nucleic acid that is expected to be present in the sample, such as a housekeeping gene that is expressed or present at a fairly standard level across samples. The internal control can be used to standardize the amount and quality of nucleic acid in the sample with that of other samples and ensure that the amplification and detection reaction is functioning. Examples of internal controls include SDH (succinate dehydrogenase), LDHA (lactate dehydrogenase A), NONO, PGK (phosphoglycerate kinase 1), PPIH, HPRT1, beta-actin, GADPH, ACTB, and 16S rRNA.

The term "diagnosis" refers to a relative probability that a subject has a disorder such as cancer or certain type of cancer (e.g., resulting from a gene fusion). Similarly, the term "prognosis" refers to a relative probability that a certain future outcome may occur in the subject. For example, in the context of the present disclosure, diagnosis can refer to classification of a cancer or the likelihood that an individual will be responsive to a particular therapy. The terms are not intended to be absolute, as will be appreciated by any one of skill in the field of medical diagnostics.

The terms "response to therapy," "response to treatment," "amelioration," and like terms refer to any reduction in the severity of symptoms. In the case of treating cancer, treatment can refer to, e.g., reducing tumor size, number of cancer cells, growth rate, metastatic activity, reducing cell death of non-cancer cells, reduced nausea and other chemotherapy or radiotherapy side effects, etc. The terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the treatment. The effect of treatment can be compared to an individual or pool of individuals not receiving the treatment (e.g., individuals having the same genetic fusion), or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "treat" and "administer," with reference to a patient, include recommending, providing, or prescribing a particular treatment to the patient, and are not limited to directly, physically treating the patient.

The term "threshold cycle" or "Ct" is a measure of relative concentration and is commonly used in real-time PCR (also referred to as qPCR). Ct refers to the intersection of an amplification curve and a threshold line. The threshold line is often set at a point when signal can be detected above background, or when an amplification reaction enters the exponential phase. Ct can be affected by concentration of target and amplification conditions, e.g., the effect of conditions on detectable labels and amplification efficiency. A higher Ct corresponds to a longer time to reach the threshold, be it due to low target concentration or inefficient amplification.

The terms "individual," "subject," "patient," and like terms are used interchangeably and refer to humans, except where indicated. Other mammals can be considered subjects, such as non-human primates, as well as rabbits, rats, mice, dogs, cats, and other mammalian species. The term does not necessarily indicate that the subject has been diagnosed with a particular disease, but typically refers to an individual under medical supervision. A patient can be seeking treatment, monitoring, adjustment or modification of an existing therapeutic regimen, etc. A patient can include individuals that have not received treatment, are currently receiving treatment, have had surgery, and those that have discontinued treatment.

The terms "label," "tag," "detectable moiety," and like terms refer to a composition detectable by spectroscopic, photochemical, biochemical, immunochemical, chemical, or other physical means. For example, useful labels include fluorescent dyes, luminescent agents, radioisotopes (e.g., $^{32}P$, $^{3}H$), electron-dense reagents, or an affinity-based moiety, e.g., a "His tag" for purification, or a "strepavidin tag" that interacts with biotin.

Unless defined otherwise, technical and scientific terms used herein have the same meaning as commonly understood by a person of ordinary skill in the art. See, e.g., Pfaffl, Methods: The ongoing evolution of qPCR, vol. 50 (2010); van Pelt-Verkuil et al. Principles and Technical Aspects of PCR Amplification, Springer (2010); Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

III. Fusion Genes

A number of cancer-associated fusion genes are known, and appear in all manner of cancers. Examples include lung cancer (e.g., non-small cell lung cancer (NSCLC), lung squamous cell carcinoma, lung adenocarcinoma), bladder carcinoma, glioblastoma, head and neck cancer, glioma, thyroid carcinoma, ovarian cancer, leukemia, lymphoma, prostate cancer, pancreatic cancer, renal cancer, and breast cancer. Cancer-associated fusion genes commonly occur where one member of the fusion is a kinase involved in a pro-growth signaling pathway, and the other member contributes to elevated or constitutive expression or signaling. This is the case for fusions of ALK, RET, and ROS1. Common fusion partners for ALK are EML4 and KIF5B. Common fusion partners for RET are KIF5B, CCDC6, and NCOA4. Several genes are known to fuse with ROS1, including CD74, EZR, TPM3, SDC4, SLC34A2, and LRIG3 (see, e.g., Yoshihara et al. (2015) *Oncogene* 34:4845).

The present compositions and methods focus on design of multiplex assays to detect ALK, RET, and ROS1 fusions. Invasive biopsy or excessive blood collection is often not feasible for cancer patients. The present compositions and methods allow for detection of several actionable gene fusions with a relatively small sample from the patient, which can be a non-invasive plasma sample.

The design of these highly multiplexed assays can vary. Where multiple ALK fusions are detected, for example, a common primer and probe that hybridize to sequences in the ALK gene near the fusion point, and primers specific for various fusion partners, can be used. Thus, for example, if 5 different ALK fusions are detected, the assay can include 15 oligonucleotides (10 primers and 5 probes) or 7 oligonucleotides (1 common primer, 1 common probe, and 5 specific primers).

In some embodiments, the multiplex assay detects 2, 3, 4, 5, 6, or 7 ALK fusions and 2, 3, 4, 5, or 6 RET fusions in a single amplification and detection reaction. In some embodiments, the multiplex assay further detects 2, 3, 4, 5, 6, 7, 8, 9, 10, 11, 12, or 13 ROS1 fusions in the same reaction. In some embodiments, the ROS1 fusions are detected in a separate amplification and detection reaction. In some embodiments, the amplification and detection reaction further includes an internal control (e.g., a housekeeping gene).

The presence of ALK, RET and ROS1 fusions indicate that a cancer patient will be responsive to a selective kinase inhibitor. These include alectinib, crizotinib, ceritinib, lorlatinib, brigatinib, cabozantinib, apatinib, vandetanib, ponatinib, lenvatinib, DS-6051b, and variants or combinations thereof. The fusion status of a patient can be monitored throughout treatment to determine if the therapeutic approach can be changed, e.g., to a different kinase inhibitor or more standard chemo- or radio-therapy.

IV. Preparation of Sample

Samples for testing for genetic fusions can be obtained from any source, but are advantageously obtained in a non-invasive manner, e.g., from blood or a blood fraction (e.g., plasma, serum, platelets, etc.). Samples for the present methods can also be taken from urine, bronchoalveolar lavage, or tissue biopsy. Methods for isolating nucleic acids from biological samples are known, e.g., as described in Sambrook, and several kits are commercially available (e.g., High Pure RNA Isolation Kit, High Pure Viral Nucleic Acid Kit, and MagNA Pure LC Total Nucleic Acid Isolation Kit from Roche).

In some embodiments, DNA is prepared, and used as template for the presently disclosed amplification and detection methods. In some embodiments, RNA is prepared. When RNA is used as template for amplification by PCR, a reverse transcription step is required to prepare cDNA. A DNA polymerase such as Taq or another thermostable polymerase can then be used to carry out amplification.

In some embodiments, the sample is RNA is isolated from blood plasma. Depending on the condition of the patient, about 1-10 mL of plasma can be obtained for testing (usually about 2 mL). Kits for isolating circulating free RNA are commercially available, e.g., from Norgen Biotek Corp or Qiagen.

As shown in the Examples, the presently disclosed methods for sample preparation and amplification/detection with custom target-specific oligos are extraordinarily sensitive, and can be used to detect gene fusion mutations from as few as about 50- and in some cases about 20-copies in a sample diluted 1:4000 in wild type RNA background. This allows for detection of fusion variants in samples where the target sequence is very rare, e.g., circulating cell-free RNA (cfRNA). Varying backgrounds of RNA and DNA in plasma do not detract from the specificity of detection even at low copy numbers.

V. Amplification and Detection

Nucleic acid amplification can be carried out using any primer-dependent method. In some embodiments, the amplification is quantitative, so that the relative or actual abundance of a given amplification target can be determined by the amount of amplification product.

DNA-based methods can be used for the presently disclosed amplification and detection methods, e.g., PCR. In some embodiments, real time or quantitative PCR is used (RTPCR or qPCR). qPCR allows for reliable detection and measurement of products generated during each cycle of PCR process. Such techniques are well known in the art, and kits and reagents are commercially available, e.g., from Roche Molecular Systems, Life Technologies, Bio-Rad, etc. See, e.g., Pfaffl (2010) *Methods: The ongoing evolution of qPCR* vol. 50. In some embodiments, the amplification and detection are carried out in the presence of a dual labeled probe (e.g., a TaqMan, CPT, LNA, or MGB probe) labeled with a quencher and a fluorophore (see, e.g., Gasparic et al. (2010) *Anal. Bioanal. Chem.* 396:2023).

In some embodiments, a preliminary reverse transcription step is carried out (also referred to as RT-PCR, not to be confused with real time PCR). See, e.g., Hierro et al. (2006) 72:7148. The term "qRT-PCR" as used herein refers to reverse transcription followed by quantitative PCR. Both reactions can be carried out in a single tube without interruption, e.g., to add reagents.

RNA-based amplification methods can also be used, e.g., transcription mediated amplification (TMA) or nucleic acid sequence based amplification (NASBA). See, e.g., Fakruddin et al. (2013) *J Pharm Bioallied Sci.* 5:245; van Deursen et al. (1999) *Nucl. Acids Res.* 27:e15; Kamisango et al. (1999) *J Clin. Microbiol.* 37:310.

Some of the oligonucleotides used in the present assays (primers and probes) include alkyl base modifications to enhance selective amplification, in particular in a multiplex format.

A probe, or one or both primers in a primer pair can be labeled with any substance or component that directly or indirectly emits or generates a detectable signal. In some embodiments, the labels are fluorophores (dyes), many of which are reported in the literature and known to those skilled in the art, and many of which are commercially available. Fluorophores are described, e.g., in Cardullo et al. (1988) Proc. Natl. Acad. Sci. USA 85: 8790; Hochstrasser et al. (1992) Biophysical Chemistry 45: 133; Selvin (1995) Methods in Enzymology 246: 300; Steinberg, Ann. Rev. Biochem., 40: 83-114 (1971); and Wang et al., Anal. Chem. 67: 1197-1203 (1995).

The following are examples of fluorophores that can be used as labels: 4-acetamido-4'-isothiocyanatostilbene-2, 2'disulfonic acid; acridine; acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate [0070] N-(4-anilino-1-naphthyl)maleimide; anthranilamide; BODIPY; Brilliant Yellow; coumarin; 7-amino-4-methylcoumarin (AMC, Coumarin 120)/7-amino-4-trifluoromethylcoumarin (Coumaran 151); cyanine dyes; cyanosine 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-(4'-dimethylaminophenylazo)benzoic acid (DABCYL); 4-dimethylaminophenylazophenyl-4'-isothiocyanate (DABITC); eosin; eosin isothiocyanate; erythrosin B; erythrosin isothiocyanate; ethidium; 5-carboxyfluorescein (FAM); 5-(4,6-dichlorotriazin-2-yl)aminofluorescein (DTAF); 2',7'-dimethoxy-4'5'-dichloro-6-carboxyfluorescein (JOE); fluorescein; fluorescein isothiocyanate; fluorescamine; IR144; IR1446; Malachite Green isothiocyanate; 4-methylumbelliferone; ortho cresolphthalein; nitrotyrosine; pararosaniline; Phenol Red; phycoerythrin (including but not limited to B and R types); o-phthaldialdehyde; pyrene; pyrene butyrate; succinimidyl 1-pyrene butyrate; quantum dots; Reactive Red 4 (Cibacron Brilliant Red 3B-A); 6-carboxy-X-rhodamine (ROX); 6-carboxyrhodamine (R6G); lissamine rhodamine B sulfonyl chloride rhodamine; rhodamine B; rhodamine 123; rhodamine X isothiocyanate; sulforhodamine B; sulforhodamine 101; sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; and lanthanide chelate derivatives.

Any of the listed fluorophores (dyes) can be used in the presently described assays to label a nucleic acid as described herein. Fluorophores can be attached by conventional covalent bonding, using appropriate functional groups on the fluorophore and/or nucleic acid.

As noted above, a dual labeled probe can be used for detection. The dual labeled probe can comprise a fluorophore, such any of the fluorophores listed above, and a quencher. Suitable quenchers include but are not limited to DDQ-I, Dabcyl, Eclipse, Iowa Black FQ, BHQ-1, QSY-7, BHQ-2, DDQ-II, Iowa Black RQ, QSY-21, and BHQ-3. For fluorophores having an emission maximum between 500 and 550 nm (e.g., FAM, TET, and HEX), a quencher with an absorption maxima between 450 and 500 nm can be selected (e.g., dabcyl or BHQ-1). For fluorophores having an emission maximum above 550 nm (e.g., rhodamine and Cy dyes), a quencher with an absorption maxima above 550 nm can be selected (e.g., BHQ-2). See, e.g., Johansson (2003) *Meth. Mol. Biol.* 335:17 for considerations in selecting dye-quencher pairs.

Detection devices are known in the art and can be selected as appropriate for the selected labels. Detection devices appropriate for quantitative PCR include the Cobas® and Light Cycler® systems (Roche), PRISM 7000 and 7300 real-time PCR systems (Applied Biosystems), etc.

VI. Kits

In some embodiments, reagents and materials for carrying out the presently disclosed methods are included in a kit. In some embodiments, the kit includes components for obtaining, storing, and/or preparing sample. Such components include, e.g., sterile needles and syringes, EDTA-lined tubes, buffers (e.g., for binding nucleic acid to, and elution from a matrix), RNase inhibitors, and/or DNase, etc.

In some embodiments, the kit includes forward primer(s) and reverse primer(s) for amplifying ALK fusion variant(s) having sequences selected from the group consisting of SEQ ID NOs:1-50, and SEQ ID NOs:52-61 and 181, respectively. In some embodiments, the kit includes probe(s) for detecting ALK fusion variant(s) having sequences selected from the group consisting of SEQ ID NOs:182-186. The forward and reverse primer sequences and probe sequences can be used together in any appropriate combination to detect any 1, 2, 3, 4, 5, 6, or 7 ALK fusion variants in any combination. In some embodiments, the kit includes forward primer(s) and reverse primer(s) for amplifying RET fusion variant(s) having sequences selected from the group consisting of SEQ ID NOs:83-145 and 187, and SEQ ID NOs:161-180, respectively. In some embodiments, the kit includes probe(s) for detecting RET fusion variant(s) having sequences selected from the group consisting of: 189-194. The forward and reverse primer sequences and probe sequences can be used together in any combination to detect any 1, 2, 3, 4, 5, or 6 RET fusion variants in any combination. In some embodiments, the kit includes forward primer(s) and reverse primer(s) for amplifying ROS1 fusion variant(s) having sequences selected from the group consisting of SEQ ID NOs:195-212, and SEQ ID NOs:213-226, respectively. In some embodiments, the kit includes probe(s) for detecting ROS1 fusion variants having sequences selected from the group consisting of: 227-230 and 51. The forward and reverse primer sequences and probe sequences can be used together in any combination to detect any 1, 2, 3, 4, 5, 6, 7, 8, 9, 10, 11, 12, or 13 ROS1 fusion variants in any combination.

In some embodiments, the kit includes a forward primer and reverse primer for amplifying an EML exon 13-ALK exon 20 fusion variant having sequences selected from the group consisting of SEQ ID NOs:1-10 and SEQ ID NOs: 52-61 and 181, respectively. In some embodiments, the kit includes a forward primer and reverse primer for amplifying an EML exon 20-ALK exon 20 fusion variant having sequences selected from the group consisting of SEQ ID NOs:11-20 and SEQ ID NOs:52-61 and 181, respectively. In some embodiments, the kit includes a forward primer and reverse primer for amplifying an EML exon 6-ALK exon 20 fusion variant having sequences selected from the group consisting of SEQ ID NOs:21-30 and SEQ ID NOs:52-61 and 181, respectively. the kit includes a forward primer and reverse primer for amplifying an EML exon 2-ALK exon 20 fusion variant having sequences selected from the group consisting of SEQ ID NOs:31-35 and SEQ ID NOs:52-61 and 181, respectively. In some embodiments, the kit includes a forward primer and reverse primer for amplifying an EML exon 18-ALK exon 20 fusion variant having sequences selected from the group consisting of SEQ ID NOs:36-40 and SEQ ID NOs:52-61 and 181, respectively. In some embodiments, the kit includes a forward primer and reverse primer for amplifying a KIF exon 24-ALK exon 20 fusion variant having sequences selected from the group consisting of SEQ ID NOs:41-45 and SEQ ID NOs:52-61 and 181, respectively. In some embodiments, the kit includes a forward primer and reverse primer for amplifying a KIF exon 17-ALK exon 20 fusion variant having sequences selected from the group consisting of SEQ ID NOs:46-50 and SEQ ID NOs:52-61 and 181, respectively. In some embodiments, the kit includes a probe for detecting an ALK fusion having a sequence selected from group consisting of SEQ ID NOs:182-186.

In some embodiments, the kit includes a forward primer and reverse primer for amplifying a KIF exon 15-RET exon 12 fusion variant having sequences selected from the group consisting of SEQ ID NOs:83-97 and SEQ ID NOs:161-180, respectively. In some embodiments, the kit includes a forward primer and reverse primer for amplifying a KIF exon 16-RET exon 12 fusion variant having sequences selected from the group consisting of SEQ ID NOs:98-107 and SEQ ID NOs:161-180, respectively. In some embodiments, the kit includes a forward primer and reverse primer for amplifying a KIF exon 22-RET exon 12 fusion variant having sequences selected from the group consisting of SEQ ID NOs:108-117 and SEQ ID NOs:161-180, respectively. In some embodiments, the kit includes a forward primer and reverse primer for amplifying a KIF exon 23-RET exon 12 fusion variant having sequences selected from the group consisting of SEQ ID NOs:118-127 and 187, and SEQ ID NOs:161-180, respectively. In some embodiments, the kit includes a forward primer and reverse primer for amplifying a CCDC exon 1-RET exon 12 fusion variant having sequences selected from the group consisting of SEQ ID NOs:128-135 and 118, and SEQ ID NOs:161-180, respectively. In some embodiments, the kit includes a forward primer and reverse primer for amplifying an NCO exon 6-RET exon 12 fusion variant having sequences selected from the group consisting of SEQ ID NOs:136-145 and SEQ ID NOs:161-180, respectively. In some embodiments, the kit includes a probe for detecting a RET fusion having a sequence selected from group consisting of SEQ ID NOs: 189-194.

In some embodiments, the kit includes a forward primer and reverse primer for amplifying a CD74 exon 6-ROS1 exon 34 fusion variant having sequences selected from the group consisting of SEQ ID NOs:195-197 and SEQ ID NOs:222-226, respectively. In some embodiments, the kit includes a forward primer and reverse primer for amplifying a CD74 exon 6-ROS1 exon 32 fusion variant having sequences selected from the group consisting of SEQ ID NOs:195-197 and SEQ ID NOs:213-215, respectively. In some embodiments, the kit includes a forward primer and reverse primer for amplifying an EZR exon 10-ROS1 exon 34 fusion variant having sequences selected from the group consisting of SEQ ID NO:208 and SEQ ID NOs:222-226, respectively. In some embodiments, the kit includes a forward primer and reverse primer for amplifying a TPM3 exon 8-ROS1 exon 35 fusion variant having sequences selected from the group consisting of SEQ ID NOs:211-212 and SEQ ID NOs:216-221, respectively. In some embodiments, the kit includes a forward primer and reverse primer for amplifying an SDC4 exon 4-ROS1 exon 34 fusion variant having sequences selected from the group consisting of SEQ ID NOs:200-202 and SEQ ID NOs:222-226, respectively. In some embodiments, the kit includes a forward primer and reverse primer for amplifying an SDC4 exon 2-ROS1 exon 32 fusion variant having sequences selected from the group consisting of SEQ ID NOs:198-199 and SEQ ID NOs:213-215, respectively. In some embodiments, the kit includes a forward primer and reverse primer for amplifying an SDC4 exon 2-ROS1 exon 34 fusion variant having sequences selected from the group consisting of SEQ ID NOs:198-199 and SEQ ID NOs:222-226, respectively. In some embodiments, the kit includes a forward primer and reverse primer for amplifying an SDC4 exon 4-ROS1 exon 32 fusion variant having sequences selected from the group consisting of SEQ ID NOs:200-202 and SEQ ID NOs:213-215, respectively. In some embodiments, the kit includes a forward primer and reverse primer for amplifying an SLC34A2 exon 13-ROS1 exon 34 fusion variant having sequences selected from the group consisting of SEQ ID NOs:203-205 and SEQ ID NOs:222-226, respectively. In some embodiments, the kit includes a forward primer and reverse primer for amplifying an SLC34A2 exon 13-ROS1 exon 32 fusion variant having sequences selected from the group consisting of SEQ ID NOs:203-205 and SEQ ID NOs:213-215, respectively. In some embodiments, the kit includes a forward primer and reverse primer for amplifying an SLC34A2 exon 4-ROS1 exon 32 fusion variant having sequences selected from the group consisting of SEQ ID NOs:206-207 and SEQ ID NOs:213-215, respectively. In some embodiments, the kit includes a forward primer and reverse primer for amplifying an SLC34A2 exon 4-ROS1 exon 34 fusion variant having sequences selected from the group consisting of SEQ ID NOs:206-207 and SEQ ID NOs:222-226, respectively. In some embodiments, the kit includes a forward primer and reverse primer for amplifying an LRIG3 exon 16-ROS1 exon 35 fusion variant having sequences selected from the group consisting of SEQ ID NOs:209-210 and SEQ ID NOs:216-221, respectively.

In some embodiments, each of the primer sets is packaged in separate tubes, e.g., to be added in ratios to be determined by the user. In some embodiments, one or more or all of the primer sets are packaged in a single tube with predetermined ratios.

The kit can also include enzymes, such as reverse transcriptase and or DNA polymerase. In some embodiments, the DNA polymerase is a thermostable DNA polymerase capable of amplifying in thermocycling conditions, e.g., Taq or a Taq derivative. In some embodiments, the kit includes dNTPs. In some embodiments, the kit includes buffers conducive to polymerization/amplification by the selected polymerases.

In some embodiments, the kit includes controls, e.g., a polynucleotide that is wild type at the genetic fusion to be detected (i.e., no genetic fusion), or a polynucleotide that includes the genetic fusion to be detected.

The kit can also include consumables such as sample tubes or vials; reaction containers (e.g., tubes, multiwell plates, microfluidic chips or chambers, etc), as well as directions for use or reference to a website.

VII. Examples

A. Example 1: Multiplex Assays for Detection of ALK, RET, and ROS1 Fusion Panel

In this example, we tested a multiplex, quantitative RT-PCR method to detect ALK, RET, and ROS1 fusions (ALK/RET/ROS1 panel). Four different sets of primers and probes are used in a single-tube (or vessel, well, chamber, compartment) assay to reduce the amount of sample needed to achieve measurable, reliable results. These four sets correspond to (i) ALK (detected with one or more probes labeled with a first label), (ii) RET (detected with one or more probes labeled with a second label), (iii) ROS1 (detected with one or more probes labeled with a third label), and (iv) an internal control (detected with a probe labeled with a forth label). The labels can be selected from those disclosed herein and in some embodiments are distinguishable from one other. In the present example, ALK fusions are detected with a FAM-labeled probe, RET fusions are detected with a HEX-labeled probe, ROS1 fusions are detected with a JA270-labeled probe, and the internal control is detected with a Cy5.5-labeled probe.

The coverage of the highly multiplexed assay is shown in Table 1 with the fusion variant number indicated in parenthesis.

TABLE 1

| Label | Gene | Fusion | Coverage | Oligonucleotides |
|---|---|---|---|---|
| FAM | ALK | EML4 exon 13-ALK exon 20 (V1) | 7 fusions | 15 primers |
|  |  | EML4 exon 20-ALK exon 20 (V2) | 94% ALK fusions | 2 probes |
|  |  | EML4 exon 6a/b-ALK exon 20 (V3) |  |  |
|  |  | EML4 exon 2-ALK exon 20 (V5) |  |  |
|  |  | EML4 exon 18-ALK exon 20 (V8) |  |  |
|  |  | KIF5B exon 17-ALK exon 20 (V6) |  |  |
|  |  | KIF5B exon 24-ALK exon 20 (V7) |  |  |
| HEX | RET | KIF5B exon 15-RET exon 12 (V1) | 6 fusions |  |
|  |  | KIF5B exon 16-RET exon 12 (V2) | 97% RET fusions |  |
|  |  | KIF5B exon 22-RET exon 12 (V3) |  |  |
|  |  | KIF5B exon 23-RET exon 12 (V4) |  |  |
|  |  | CCDC6 exon 1-RET exon 12 (V8) |  |  |
|  |  | NCOA4 exon 6-RET exon 12 (V9) |  |  |
| JA270 | ROS1 | CD74 exon 6-ROS1 exon 34 (V2) | 12 fusions | 11 primers |
|  |  | CD74 exon 6-ROS1 exon 32 (V1) | 95% ROS1 fusions | 3 probes |
|  |  | EZR exon 10-ROS1 exon 34 (V10) |  |  |
|  |  | TPM3 exon 8-ROS1 exon 35 (V13) |  |  |
|  |  | SDC4 exon 4-ROS1 exon 34 (V5) |  |  |
|  |  | SDC4 exon 2-ROS1 exon 32 (V3) |  |  |
|  |  | SDC4 exon 2-ROS1 exon 34 (V14) |  |  |
|  |  | SDC4 exon 4-ROS1 exon 32 (V4) |  |  |
|  |  | SLC34A2 exon 13-ROS1 exon 34 (V7) |  |  |
|  |  | SLC34A2 exon 13-ROS1 exon 32 (V6) |  |  |
|  |  | SLC34A2 exon 4-ROS1 exon 32 (V8) |  |  |
|  |  | SLC34A2 exon 4-ROS1 exon 34 (V9) |  |  |
|  |  | LRIG3 exon 16-ROS1 exon 35 (V11) |  |  |

TABLE 1-continued

| Label | Gene | Fusion | Coverage | Oligonucleotides |
|---|---|---|---|---|
| CY5.5 | IC | IC | N/A | 2 primers<br>1 probe |

The multiplex may include various gene fusion detection combinations, and in some embodiments, fewer fusions are assayed and detected. An example of an assay format for detection ALK and RET fusions is shown in Table 2. Fusions in ROS1 can be detected separately, or in a parallel assay, for example, as shown in Table 3.

TABLE 2

| Label | Gene | Fusion | Coverage | Oligonucleotides |
|---|---|---|---|---|
| FAM | ALK | EML4 exon 13-ALK exon 20 (V1)<br>EML4 exon 20-ALK exon 20 (V2)<br>EML4 exon 6a/b-ALK exon 20 (V3)<br>EML4 exon 2-ALK exon 20 (V5)<br>EML4 exon 18-ALK exon 20 (V8)<br>KIF5B exon 17-ALK exon 20 (V6)<br>KIF5B exon 24-ALK exon 20 (V7) | 7 fusions<br>94% ALK fusions | 15 primers<br>2 probes |
| HEX | RET | KIF5B exon 15-RET exon 12 (V1)<br>KIF5B exon 16-RET exon 12 (V2)<br>KIF5B exon 22-RET exon 12 (V3)<br>KIF5B exon 23-RET exon 12 (V4)<br>CCDC6 exon 1-RET exon 12 (V8)<br>NCOA4 exon 6-RET exon 12 (V9) | 6 fusions<br>97% RET fusions | |
| CY5.5 | IC | IC | N/A | 2 primers<br>1 probe |

TABLE 3

| Label | Gene | Fusion | Coverage | Oligonucleotides |
|---|---|---|---|---|
| FAM | ROS1 | CD74 exon 6-ROS1 exon 32 (V1)<br>SDC4 exon 2-ROS1 exon 32 (V3)<br>SDC4 exon 4-ROS1 exon 32 (V4)<br>SLC34A2 exon 13-ROS1 exon 32 (V6)<br>SLC34A2 exon 4-ROS1 exon 32 (V8) | 12 fusions<br>95% ROS1 fusions | 11 primers<br>3 probes |
| HEX | ROS1 | CD74 exon 6-ROS1 exon 34 (V2)<br>EZR exon 10-ROS1 exon 34 (V10)<br>SDC4 exon 4-ROS1 exon 34 (V5)<br>SLC34A2 exon 13-ROS1 exon 34 (V7)<br>SLC34A2 exon 4-ROS1 exon 34 (V9)<br>SDC4 exon 2-ROS1 exon 34 (V14) | | |
| JA270 | ROS1 | TPM3 exon 8-ROS1 exon 35 (V13)<br>LRIG3 exon 16-ROS1 exon 35 (V11) | | |
| CY5.5 | IC | IC | N/A | 2 primers<br>1 probe |

The oligonucleotides shown in Tables 4-6 can be selected for use in the assays. The first set of forward and reverse primers amplifies across EML4-ALK and KIF5B-ALK fusions. The primers are designated with the gene name (e.g. EML for EML4), exon (e.g., 13 for exon 13), and designation (e.g., F1 for Forward 1). The symbols <t_bb_dA>, <t_bb_dC>, <t_bb_dT>, <t_bb_dG> refer to p-tert butylbenzyl modified A, C, T, and G, respectively. Forward and reverse primers can be used in single pairs or in any combination to amplify different fusion products, as will be appreciated by one of skill in the art. In the present example, the number of oligonucleotides in the reaction was minimized, as indicated in Tables 1-3. The reverse primers in all reactions served as primers for the reverse transcriptase reactions.

TABLE 4

Oligonucleotides for use in amplification and detection of ALK fusions

| Probe dye (for example) | | SEQ ID NO | Sequence |
|---|---|---|---|
| | Forward primer | | |
| FAM | EML13F1 | 1 | ACACCTGGGAAAGGACCTAAA |
| | EML13F2 | 2 | CACACCTGGGAAAGGACCTAAA |
| | EML13F3 | 3 | CCACACCTGGGAAAGGACCTA |
| | EML13F4 | 4 | CCACACCTGGGAAAGGACCT |
| | EML13F5 | 5 | CCACACCTGGGAAAGGACC |
| | EML13F6 | 6 | CCACACCTGGGAAAGGAC |
| | EML13F7 | 7 | CCCACACCTGGGAAAGGAC |
| | EML13F8 | 8 | GCCCACACCTGGGAAAGGA |
| | EML13F9 | 9 | AGCCCACACCTGGGAAAG |
| | EML13F10 | 10 | GAGCCCACACCTGGGAAA |
| | EML20F1 | 11 | CTCGGGAGACTATGAAATATTGTACT |
| | EML20F2 | 12 | TCGGGAGACTATGAAATATTGTACT |
| | EML20F3 | 13 | CGGGAGACTATGAAATATTGTACT |
| | EML20F4 | 14 | CTCGGGAGACTATGAAATATTGTAC |
| | EML20F5 | 15 | ACTCGGGAGACTATGAAATATTGTA |
| | EML20F6 | 16 | AACTCGGGAGACTATGAAATATTGTA |
| | EML20F7 | 17 | TAACTCGGGAGACTATGAAATATTGTA |
| | EML20F8 | 18 | TAACTCGGGAGACTATGAAATATTGT |
| | EML20F9 | 19 | TAACTCGGGAGACTATGAAATATTGTA |
| | EML20F10 | 20 | ACTCGGGAGACTATGAAATATTGTAC |
| | EML6F1 | 21 | AAGCATAAAGATGTCATCATCAACCAA |
| | EML6F2 | 22 | AGCATAAAGATGTCATCATCAACCAA |
| | EML6F3 | 23 | GCATAAAGATGTCATCATCAACCAA |
| | EML6F4 | 24 | CATAAAGATGTCATCATCAACCAAG |
| | EML6F5 | 25 | GCATAAAGATGTCATCATCAACCAAG |
| | EML6F6 | 26 | GCATAAAGATGTCATCATCAACCA |
| | EML6F7 | 27 | GCATAAAGATGTCATCATCAACC |
| | EML6F8 | 28 | AGCATAAAGATGTCATCATCAACC |
| | EML6F9 | 29 | AAGCATAAAGATGTCATCATCAACC |
| | EML6F10 | 30 | AAGCATAAAGATGTCATCATCAAC |
| | EML2F1 | 31 | CTCAGTGAAAAAATCAGTCTCAAG |
| | EML2F2 | 32 | CTCAGTGAAAAAATCAGTCTCAAGT |
| | EML2F3 | 33 | TCAGTGAAAAAATCAGTCTCAAGTA |
| | EML2F4 | 34 | TCAGTGAAAAAATCAGTCTCAAGTAA |
| | EML2F5 | 35 | CAGTGAAAAAATCAGTCTCAAGTAAAG |
| | EML18F1 | 36 | CAGCTCTCTGTGATGCGCTA |
| | EML18F2 | 37 | CTCTCTGTGATGCGCTACT |
| | EML18F3 | 38 | TCTCTGTGATGCGCTACTCAA |
| | EML18F4 | 39 | GCTCTCTGTGATGCGCTAC |
| | EML18F5 | 40 | CTGTGATGCGCTACTCAATAG |
| | KIF24F1 | 41 | AGAAGAGGGCATTCTGCACA |
| | KIF24F2 | 42 | GAGGGCATTCTGCACAGA |
| | KIF24F3 | 43 | GAGGGCATTCTGCACAGAT |
| | KIF24F4 | 44 | GAAGAGGGCATTCTGCACAG |
| | KIF24F5 | 45 | GGGCATTCTGCACAGATTG |
| | KIF17F1 | 46 | GAACTAGTCCAGCTTCGAGCA |
| | KIF17F2 | 47 | TGAAGAACTAGTCCAGCTTCGA |
| | KIF17F3 | 48 | CTAGTCCAGCTTCGAGCACAA |
| | KIF17F4 | 49 | AAGAACTAGTCCAGCTTCGAG |
| | KIF17F5 | 50 | GTCCAGCTTCGAGCACAAG |
| | Reverse primer | | |
| | ALK20R1 | 52 | GCTCTGCAGCTCCATCTG |
| | ALK20R2 | 53 | GGCTCTGCAGCTCCATCT |
| | ALK20R3 | 54 | GGGCTCTGCAGCTCCATC |
| | ALK20R4 | 55 | GGGCTCTGCAGCTCCAT |
| | ALK20R5 | 56 | GGGCTCTGCAGCTCCA |
| | ALK20R6 | 57 | TGCAGCTCCATCTGCATGG |
| | ALK20R7 | 58 | GCAGCTCCATCTGCATGG |
| | ALK20R8 | 59 | CAGCTCCATCTGCATGGC |
| | ALK20R9 | 60 | AGCTCCATCTGCATGGC |
| | ALK20R10 | 61 | GCTCCATCTGCATGGCT |
| | ALK20R11 | 181 | TGCAGCTCCATCTGCATGGCT TGCAGCTCCATCTGCATGG<t_bb_dC>T |
| | Probe | | |
| | ALK20RP9_Q6 | 182 | <DYE-Thr>CCGCCG<BHQ_2>GAAGCACCAGGAGC |
| | ALK20P4 | 183 | <DYE-Thr>TACCGCC<BHQ_2>GGAAGCACCAGGAGCTGCA |
| | ALK20P5 | 184 | <DYE-Thr>TACCGCC<BHQ_2>GGAAGCACCAGGAGCTGC |

TABLE 4-continued

Oligonucleotides for use in amplification and detection of ALK fusions

| Probe dye (for example) | | SEQ ID NO | Sequence |
|---|---|---|---|
| | ALK20P6 | 185 | \<DYE-Thr>TACCGCC<br>\<BHQ_2>GGAAGCACCAGGAGCTG |
| | ALK20P7 | 186 | \<DYE-Thr>TACCGCC<br>\<BHQ_2>GGAAGCACCAGGAGCT |

TABLE 5

Oligonucleotides for use in amplification and detection of RET fusions

| Probe dye (for example) | | SEQ ID NO | Sequence |
|---|---|---|---|
| | Forward primer | | |
| HEX | KIF15F1 | 83 | GAATTGCTGTGGGAAATAATGATG |
| | KIF15F2 | 84 | GAATTGCTGTGGGAAATAATGAT |
| | KIF15F3 | 85 | ATTGCTGTGGGAAATAATGATGTAAAG |
| | KIF15F4 | 86 | TTGCTGTGGGAAATAATGATGTAAAG |
| | KIF15F5 | 87 | TGCTGTGGGAAATAATGATGTAAAG |
| | KIF15F6 | 88 | GCTGTGGGAAATAATGATGTAAAG |
| | KIF15F7 | 89 | GAATTGCTGTGGGAAATAATGATGTAAA |
| | KIF15F8 | 90 | GAATTGCTGTGGGAAATAATGATGTAA |
| | KIF15F9 | 91 | AATTGCTGTGGGAAATAATGATGTAAA |
| | KIF15F10 | 92 | ATTGCTGTGGGAAATAATGATGTAAA |
| | KIF15F11 | 93 | ATTGCTGTGGGAAATAATGATGTAA |
| | KIF15F12 | 94 | AATTGCTGTGGGAAATAATGATGTA |
| | KIF15F13 | 95 | ATTGCTGTGGGAAATAATGATGTA |
| | KIF15F14 | 96 | GAATTGCTGTGGGAAATAATGATGTA |
| | KIF15F15 | 97 | GAATTGCTGTGGGAAATAATGATGT |
| | KIF16F1 | 98 | CATGTCAGCTTCGTATCTCTCAA |
| | KIF16F2 | 99 | ATGTCAGCTTCGTATCTCTCAA |
| | KIF16F3 | 100 | CATGTCAGCTTCGTATCTCTCA |
| | KIF16F4 | 101 | GCATGTCAGCTTCGTATCTCTC |
| | KIF16F5 | 102 | CATGTCAGCTTCGTATCTCTC |
| | KIF16F6 | 103 | GCATGTCAGCTTCGTATCTCT |
| | KIF16F7 | 104 | GCATGTCAGCTTCGTATCTC |
| | KIF16F8 | 105 | CAGCATGTCAGCTTCGTATC |
| | KIF16F9 | 106 | TAGCAGCATGTCAGCTTCGTA |
| | KIF16F10 | 107 | AGCAGCATGTCAGCTTCG |
| | KIF22F1 | 108 | AGGACCTGGCTACAAGAGTTAA |
| | KIF22F2 | 109 | GGACCTGGCTACAAGAGTTAA |
| | KIF22F3 | 110 | GGACCTGGCTACAAGAGTTAAA |
| | KIF22F4 | 111 | AGGACCTGGCTACAAGAGTTAAA |
| | KIF22F5 | 112 | AGGACCTGGCTACAAGAGTTA |
| | KIF22F6 | 113 | GGACCTGGCTACAAGAGTTA |
| | KIF22F7 | 114 | GACCTGGCTACAAGAGTTAAAAG |
| | KIF22F8 | 115 | ACCTGGCTACAAGAGTTAAAAG |
| | KIF22F9 | 116 | AGGACCTGGCTACAAGAGTT |
| | KIF22F10 | 117 | GGACCTGGCTACAAGAGTT |
| | KIF23F1 | 118 | TTGAACAGCTCACTAAAGTGCACAAA |
| | KIF23F2 | 119 | TGAACAGCTCACTAAAGTGCACAAA |
| | KIF23F3 | 120 | GAACAGCTCACTAAAGTGCACAAA |
| | KIF23F4 | 121 | AACAGCTCACTAAAGTGCACAAA |
| | KIF23F5 | 122 | ACAGCTCACTAAAGTGCACAAA |
| | KIF23F6 | 123 | GAACAGCTCACTAAAGTGCACAA |
| | KIF23F7 | 124 | AACAGCTCACTAAAGTGCACAA |
| | KIF23F8 | 125 | ACAGCTCACTAAAGTGCACAA |
| | KIF23F9 | 126 | GAACAGCTCACTAAAGTGCACA |
| | KIF23F10 | 127 | AACAGCTCACTAAAGTGCACA |
| | KIF23F13 | 187 | TTGAACAGCTCACTAAAGTGCA |
| | CCDC1F1 | 128 | TGCGCAAAGCCAGCGT |
| | CCDC1F2 | 129 | CGACCTGCGCAAAGCCA |
| | CCDC1F3 | 130 | GACCTGCGCAAAGCCAG |
| | CCDC1F4 | 131 | CCTGCGCAAAGCCAGC |
| | CCDC1F5 | 132 | ACCTGCGCAAAGCCAGC |
| | CCDC1F6 | 133 | CTGCGCAAAGCCAGCGT |
| | CCDC1F7 | 134 | GACCTGCGCAAAGCCAGC |
| | CCDC1F8 | 135 | CGACCTGCGCAAAGCC |
| | CCDC1F14 | 188 | CAAAGCCAGCGTGACCA |
| | NCO6F1 | 136 | TGTATCTCCATGCCAGAGCAG |
| | NCO6F2 | 137 | GTATCTCCATGCCAGAGCAG |

TABLE 5-continued

Oligonucleotides for use in amplification and detection of RET fusions

| Probe dye (for example) | | SEQ ID NO | Sequence |
|---|---|---|---|
| | NCO6F3 | 138 | CTGTATCTCCATGCCAGAGCA |
| | NCO6F4 | 139 | GCTGTATCTCCATGCCAGAG |
| | NCO6F5 | 140 | GGCTGTATCTCCATGCCAGA |
| | | | GGCTGTATCTCCATGCCAG\<Lbb_dA\> |
| | NCO6F6 | 141 | GGCTGTATCTCCATGCCAG |
| | NCO6F7 | 142 | AGGCTGTATCTCCATGCCA |
| | NCO6F8 | 143 | GAGGCTGTATCTCCATGCCA |
| | NCO6F9 | 144 | AGAGGCTGTATCTCCATGC |
| | NCO6F10 | 145 | GAGAGGCTGTATCTCCATGC |
| | Reverse primer | | |
| | RET12R1 | 161 | AGAGTTTTTCCAAGAACCAAGTTCT |
| | RET12R2 | 162 | CTAGAGTTTTTCCAAGAACCAAGTTCT |
| | RET12R3 | 163 | CTAGAGTTTTTCCAAGAACCAAGTTC |
| | RET12R4 | 164 | CTAGAGTTTTTCCAAGAACCAAGTT |
| | RET12R5 | 165 | CTAGAGTTTTTCCAAGAACCAAGT |
| | RET12R6 | 166 | CTAGAGTTTTTCCAAGAACCAAG |
| | RET12R7 | 167 | TAGAGTTTTTCCAAGAACCAAGTCTT |
| | RET12R8 | 168 | GAGTTTTTCCAAGAACCAAGTTCTT |
| | RET12R9 | 169 | AGTTTTTCCAAGAACCAAGTTCTT |
| | RET12R10 | 170 | GTTTTTCCAAGAACCAAGTTCTT |
| | RET12R11 | 171 | TAGAGTTTTTCCAAGAACCAAGTTCT |
| | RET12R12 | 172 | TAGAGTTTTTCCAAGAACCAAGTTC |
| | RET12R13 | 173 | AGAGTTTTTCCAAGAACCAAGTTC |
| | RET12R14 | 174 | AGAGTTTTTCCAAGAACCAAGTT |
| | RET12R15 | 175 | AGAGTTTTTCCAAGAACCAAGT |
| | RET12R16 | 176 | CTCCTAGAGTTTTTCCAAGAACCAA |
| | RET12R17 | 177 | CTCCTAGAGTTTTTCCAAGAACCA |
| | RET12R18 | 178 | TCCTAGAGTTTTTCCAAGAACCAA |
| | RET12R19 | 179 | CCTAGAGTTTTTCCAAGAACCAA |
| | RET12R20 | 180 | GAGTTTTTCCAAGAACCAAGTTCT |
| | Probe | | |
| | RET12P3_HEX | 189 | \<DYE_Thr\>ATCCAAA\<BHQ_2\>GTGGGAATT CCCTCGGAAGAAC |
| | RET12P4_HEX | 190 | \<DYE_Thr\>CCAAAGT\<BHQ_2\>GGGAATT CCCTCGGAAGAAC |
| | RET12P8_HEX | 191 | \<DYE_Thr\>TCCAAAG\<BHQ_2\>TGGGAATT CCCTCGGAAGAA |
| | RET12P14_HEX | 192 | \<DYE_Thr\>CCAAAGT\<BHQ_2\>GGGAATT CCCTCGGAAGAACTT |
| | RET12P18_HEX | 193 | \<DYE_Thr\>TCCAAAG\<BHQ_2\>TGGGAATT CCCTCGGAAGAACTT |
| | RET12P13_HEX | 194 | \<DYE_Thr\>ATCCAAA\<BHQ_2\>GTGGGAATT CCCTCGGAAGAACTT |

TABLE 6

Oligonucleotides for use in amplification and detection of ROS1 fusions

| Probe dye (for example) | | SEQ ID NO | Sequence |
|---|---|---|---|
| | Forward primer | | |
| JA270 | CD74ex6F2 | 195 | CACTGACGCTCCACCGAA |
| | CD74ex6F1 | 196 | AAGCCCACTGACGCTCCA |
| | CD74ex6F3 | 197 | ACTGACGCTCCACCGAAA |
| | SDC4ex2F1 | 198 | GAGCTGTCTGGCTCTGG\<t_BB_dA\> |
| | SDC4ex2F2 | 199 | TGTCTGGCTCTGGAGATCT |
| | | | TGTCTGGCTCTGGAGAT\<t_bb_dC\>T |
| | SDC4ex4F1 | 200 | TTGAGAGAACGGAGGTCCT |
| | SDC4exF2 | 201 | TGAGAGAACGGAGGTCCT |
| | SDC4ex4F3 | 202 | TTGAGAGAACGGAGGTCCTG |
| | SLC34A2ex13F1 | 203 | ATAACCATTAGCAGAGAGGCT |
| | SLC34A2ex13F2 | 204 | AACCATTAGCAGAGAGGCTCA |
| | SLC34A2ex13F3 | 205 | ATAACCATTAGCAGAGAGGCT |
| | SLC34A2ex4F1 | 206 | AGTAGCGCCTTCCAGCT |
| | SLC34A2ex4F2 | 207 | GCCTTCCAGCTGGTTGGA |
| | EZRex10F2 | 208 | GAAGACAAAGAAGGCAGAGAGA |

TABLE 6-continued

Oligonucleotides for use in amplification and detection of ROS1 fusions

| Probe dye (for example) | | SEQ ID NO | Sequence |
|---|---|---|---|
| | LRIG3ex16F1 | 209 | TTCTTACCACAACATGACAGTAGT |
| | LRIG3ex16F2 | 210 | TCTTACCACAACATGACAGTAGTG |
| | TPM3ex8F1 | 211 | GAAAAGACAATTGATGACCTGGA |
| | | | GAAAAGACAATTGATGACCTGG<t_BB_dA> |
| | TPM3ex8F5 | 212 | AAGCTGGAAAAGACAATTGATGAC |
| Reverse primer | | | |
| | ROS1ex32R1 | 213 | GTATTGAATTTTTACTCCCTTCTAGTAATTTG |
| | ROS1ex32R2 | 214 | GTATTGAATTTTTACTCCCTTCTAGTAATTT |
| | ROS1ex32R3 | 215 | GTATTGAATTTTTACTCCCTTCTAGTAATT |
| | ROS1ex35R1 | 216 | TATAAGCACTGTCACCCCTT |
| | ROS1ex35R2 | 217 | ATAAGCACTGTCACCCCTT |
| | ROS1ex35R3 | 218 | TATAAGCACTGTCACCCCT |
| | ROS1ex35R4 | 219 | CTTTGTCTTCGTTTATAAGCACTGTCA |
| | ROS1ex35R5 | 220 | AACTCTTTGTCTTCGTTTATAAGCACTGT |
| | ROS1ex35R6 | 221 | AGCCAACTCTTTGTCTTCGTTTATAAGCA |
| | ROS1ex34LArev1 | 222 | CAGTGGGATTGTAACAACCAGAAAT |
| | ROS1ex34LArev2 | 223 | GTCAGTGGGATTGTAACAACCAGA |
| | ROS1ex34LArev3 | 224 | GTCAGTGGGATTGTAACAACCA |
| | ROS1ex34LArev4 | 225 | CAGTGGGATTGTAACAACCAGAAA |
| | ROS1ex34LArev5 | 226 | CAGTGGGATTGTAACAACCAGAA |
| Probe | | | |
| | ROS1EX32P2 | 227 | <DYE_Thr>TGGAGTCCCAAA<BHQ_2> |
| | | | TAAACCAGGCATTCCCA |
| | ROS1EX34P1 | 228 | <DYE_Thr>TGATTTTTGGAT<BHQ_2> |
| | | | ACCAGAAACAAGTTTCATAC |
| | ROS1EX32P3 | 229 | <DYE_Thr>TGGAGTC<BHQ_2> |
| | | | CCAAATAAACCAGGC<t_BB_dA>TTCCCA |
| | ROS1EX34P3 | 230 | <DYE_Thr>TGATTTT<BHQ_2> |
| | | | TGGATACCAGAAACAAGTTTCATAC |
| | ROS1EX35P1 | 51 | <DYE_Thr>TCTGGCATAGAA<BHQ_2> |
| | | | GATTAAAGAATCAAAAAAGTGCCAAG |

We have tested this method using RNA from EML4-ALK positive cell lines NCI-H2228 and EML4-ALK Fusion Variant 1 cell line from Horizon Discovery, CCDC6-RET cell line LC2AD, as well as from NSCLC formalin fixed paraffin embedded tissue (FFPET) and plasma specimens.

In the case of plasma, we extracted cfRNA using the Roche High Pure FFPET RNA extraction kit with MagNA Pure Lysis Buffer and Esperase enzyme. Because the yield of cfRNA is too low to be measured accurately, we input a fixed volume (1/24 of total) of the extracted plasma cfRNA into the qRT-PCR.

The reaction conditions were as follows. For each reaction, 25 uL of input RNA was added to a RT-PCR reaction mix comprising forward and reverse primers, labeled probe, buffer, dUTP, dTTP, dATP, dGTP, UNG, and Z05 enzyme to a final volume of 50 uL. The reactions were run in multiplex, each with primers and probes specific for every fusion variant indicated in Table 1.

Results were confirmed using a Next Generation Sequencing assay that detects the fusion variants covered in the qRT-PCR assay.

Maximum Ct (threshold cycle) was set at 38, meaning that a signal must be detectable over background within a Ct of 38. Data is shown in FIGS. 1A, 1B, 1C, and 1D. The input RNA for each reaction was known to have the indicated fusion variant. Each reaction was repeated three times.

FIG. 1A shows that each ALK fusion variant is detectable at 50 copies. FIG. 1B shows that each RET fusion variant is detectable at 50 copies. FIG. 1C shows that each ROS1 fusion variant is detectable at 50 copies. FIG. 1D shows that the reaction efficiency and input was equivalent, as indicated by the Internal Control Ct's.

B. Example 2: Sensitivity of ALK and RET Fusions in Titered Transcripts

We tested the multiplex qRT-PCR for the limit of detection of the ALK and RET fusion variants shown in Example 1, Table 1. We tested the multiplex assay by titering ALK or RET fusion positive transcripts into 0.1 ng Universal Human RNA (UHR) at 250, 100, 50, or 25 copies. The amplification and detection reactions were repeated 3 times.

As shown in FIG. 2, all of the ALK and RET fusion variants tested was detectable down to 25 copies.

C. Example 3: Linearity Studies and Further Limit of Detection (LOD) Studies

Figure 3:
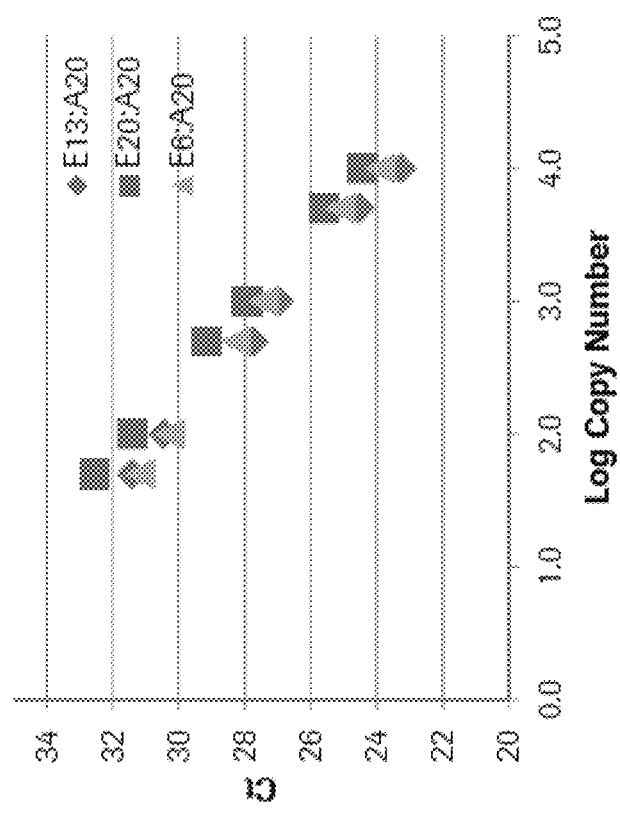
FIG. 3 shows linearity data for representative ALK fusion variants. Each representative ALK fusion RNA transcript was tested in 0.5 ng Universal Human RNA (UHR) background. Five different copy number levels of transcript were spiked into the UHR: 10000, 5000, 1000, 500, 100, and 50. Three replicates were run for each level, and copy number estimated by ddPCR.
Figure 4:
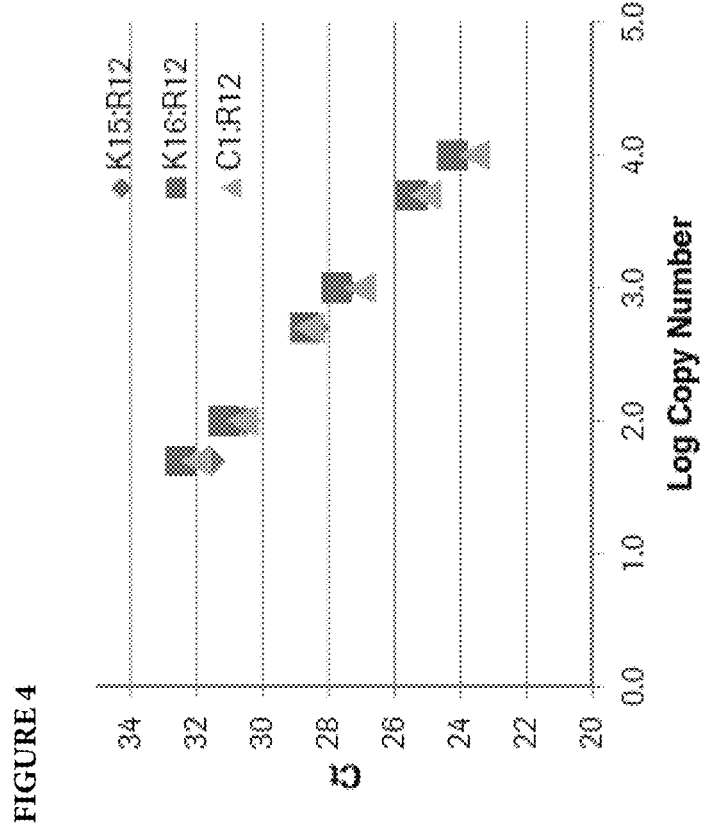
FIG. 4 shows linearity data for representative RET fusion variants. Each representative RET fusion RNA transcript was tested in 0.5 ng UHR background. Five different copy number levels of transcript were spiked into the UHR: 10000, 5000, 1000, 500, 100, and 50. Three replicates were run for each level, and copy number estimated by ddPCR.
Figure 5:
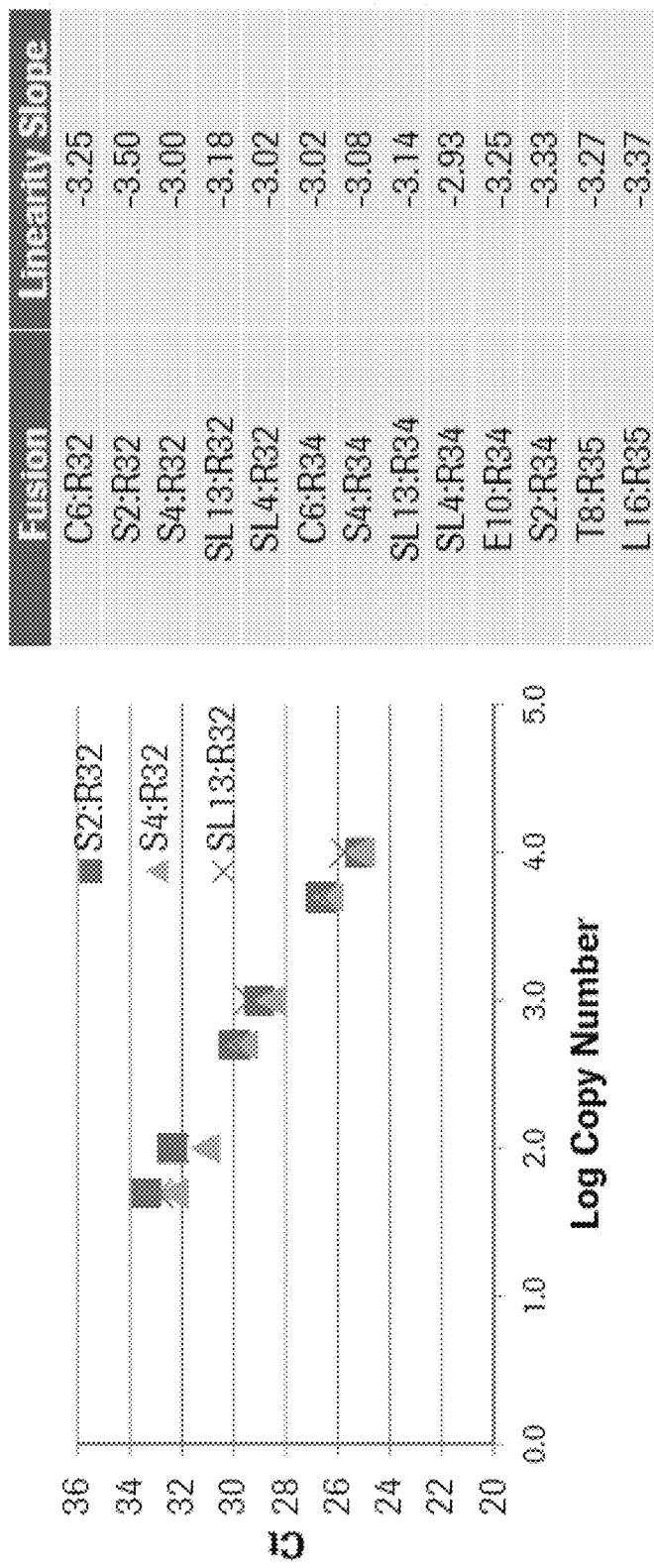
FIG. 5 shows linearity data for representative ROS1 fusion variants. Each representative ROS1 fusion RNA transcript was tested in 0.5 ng UHR background. Five different copy number levels of transcript were spiked into the UHR: 10000, 5000, 1000, 500, 100, and 50. Three replicates were run for each level, and copy number estimated by ddPCR.

Further studies were carried out to determine the linearity of detection for ALK, RET, and ROS1 fusions, as shown and described in FIGS. 3-5.

Figure 6:
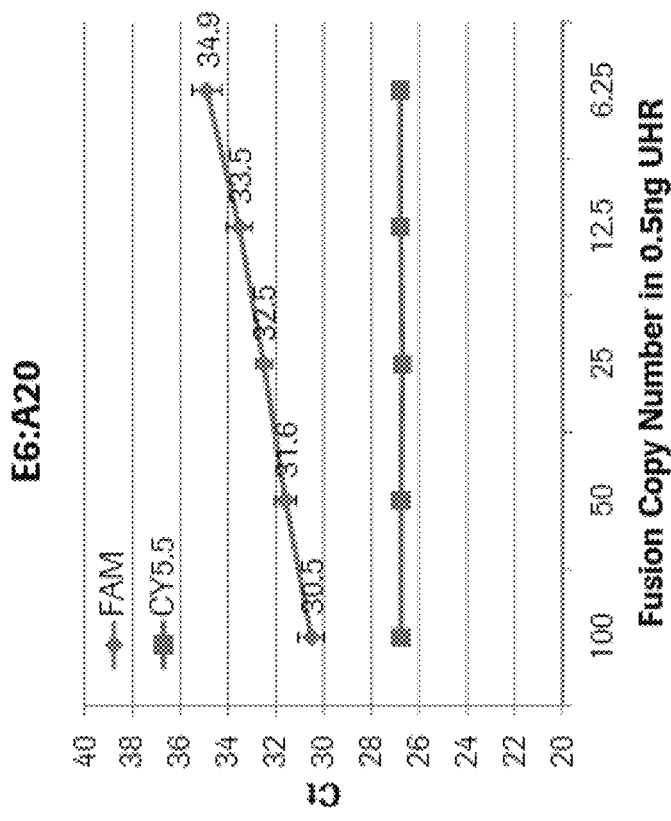
FIG. 6 shows LOD data for a representative ALK fusion variant. Representative ALK fusion RNA transcript E6:A20 was tested in 0.5 ng UHR background. UHR background was increased from 0.1 ng to ensure assay robustness. Five different copy number levels of transcript were spiked into the UHR: 100, 50, 25, 12.5, and 6.25. Three replicates were run for each level, and copy number estimated by ddPCR.
Figure 7:
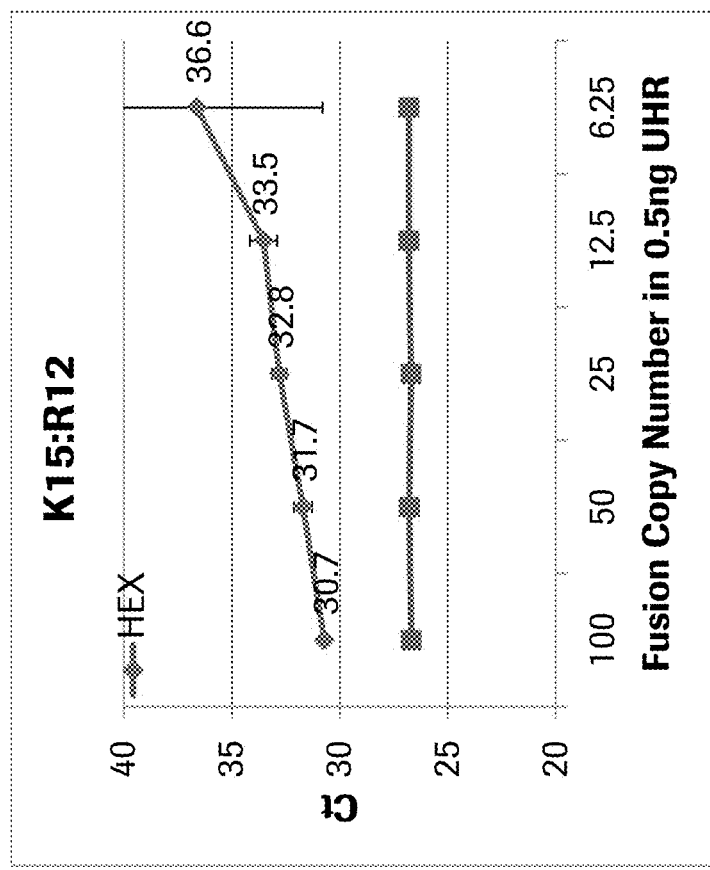
FIG. 7 shows LOD data for a representative RET fusion variant. Representative RET fusion RNA transcript K15:R12 was tested in 0.5 ng UHR background. UHR background was increased from 0.1 ng to ensure assay robustness. Five different copy number levels of transcript were spiked into the UHR: 100, 50, 25, 12.5, and 6.25. Three replicates were run for each level, and copy number estimated by ddPCR.
Figure 8:
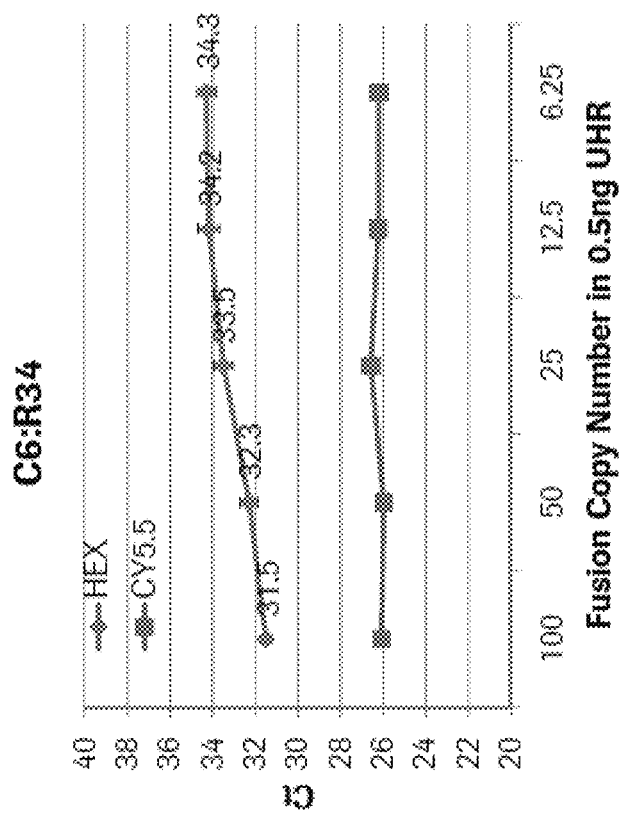
FIG. 8 shows LOD data for a representative ROS1 fusion variant. Representative ROS1 fusion RNA transcript C6:R34 was tested in 0.5 ng UHR background. UHR background was increased from 0.1 ng to ensure assay robustness. Five different copy number levels of transcript were spiked into the UHR: 100, 50, 25, 12.5, and 6.25. Three replicates were run for each level, and copy number estimated by ddPCR.

Sensitivity, or Limit of Detection (LOD) studies are shown and described in FIGS. 6-8. The LOD for each assay is shown in Tables 7 and 8. All 7 ALK, 6 RET, and 13 ROS1 fusion variants are detectable down to less than 10 copies. The predominant fusion variants are marked with an *.

TABLE 7

| Fusion | Hit Rate | LOD for 95% Probability |
|---|---|---|
| E13:A20* | 12/12 all levels tested | <6.25 copies |
| E20:A20* | 12/12 all levels tested | <6.25 copies |
| E6:A20* | 12/12 all levels tested | <6.25 copies |
| E2:A20 | 11/12 at 6.25 copies | 6.45 copies |

TABLE 7-continued

| Fusion | Hit Rate | LOD for 95% Probability |
|---|---|---|
| K17:A20 | 12/12 at 6.25 copies (11/12 at 12.5 copies) | 4.78 copies |
| K24:A20 | 12/12 all levels tested | <6.25 copies |
| E18:A20 | 12/12 all levels tested | <6.25 copies |
| K15:R12* | 11/12 at 6.25 copies | 6.45 copies |
| K16:R12* | 11/12 at 6.25 copies | 6.45 copies |
| K22:R12 | 12/12 all levels tested | <6.25 copies |
| K23:R12 | 11/12 at 6.25 copies | 6.45 copies |
| C1:R12* | 12/12 all levels tested | <6.25 copies |
| N6:R12 | 12/12 all levels tested | <6.25 copies |

TABLE 8

| Fusion variant | Hit Rate | LOD for 95% Probability |
|---|---|---|
| C6:R32 | 12/12 all levels tested | <6.25 copies |
| C6:R34* | 12/12 all levels tested | <6.25 copies |
| SD2:R32 | 11/12 at 6.25 and 12.5 copies | 11.07 copies |

TABLE 8-continued

| Fusion variant | Hit Rate | LOD for 95% Probability |
|---|---|---|
| SD4:R34 | 12/12 all levels tested | <6.25 copies |
| SL13:R32 | 12/12 all levels tested | <6.25 copies |
| SL13:R34 | 12/12 all levels tested | <6.25 copies |
| SL4:R32 | 12/12 all levels tested | <6.25 copies |
| SL4:R34 | 11/12 at 6.25 copies | 6.45 copies |
| E10:R34* | 11/12 at 6.25 copies | 6.45 copies |
| L16:R35 | 11/12 at 12.5 copies; 12/12 at 6.25 copies | 4.78 copies |
| T8:R35 | 12/12 all levels tested | <6.25 copies |
| SD2:R34 | 12/12 all levels tested | <6.25 copies |

While the invention has been described in detail with reference to specific examples, it will be apparent to one skilled in the art that various modifications can be made within the scope of this invention. Thus the scope of the invention should not be limited by the examples described herein. All patents, publications, websites, Genbank (or other database) entries disclosed herein are incorporated by reference in their entireties.

We claim:

1. A multiplex assay composition comprising:
   A. at least one primer set and probe that specifically amplify and detect at least one ALK fusion gene, wherein:
      (i) the at least one primer set that specifically amplifies the at least one ALK fusion gene comprises a forward primer comprising SEQ ID NO:1 and a reverse primer comprising SEQ ID NO:52; and
      (ii) the probe that specifically detects the at least one ALK fusion gene comprises SEQ ID NO:182 and is labeled with at least one non-naturally occurring moiety;
   B. at least one primer set and probe that specifically amplify and detect at least one RET fusion gene, wherein:
      (i) the at least one primer set that specifically amplifies the at least one RET fusion gene comprises a forward primer comprising SEQ ID NO:83 and a reverse primer comprising SEQ ID NO:161; and
      (ii) the probe that specifically detects the at least one RET fusion gene comprises SEQ ID NO:189 and is labeled with at least one non-naturally occurring moiety;
   C. at least one primer set and probe that specifically amplify and detect at least one ROS1 fusion gene, wherein:
      (i) the at least one primer set that specifically amplifies the at least one ROS1 fusion gene comprises a forward primer comprising SEQ ID NO:195 and a reverse primer comprising SEQ ID NO:213; and
      (ii) the probe that specifically detects the at least one ROS1 fusion gene comprises SEQ ID NO:227 and is labeled with at least one non-naturally occurring moiety; and
   D. a primer set and probe that specifically amplify and detect an internal control, wherein the probe that specifically detects the internal control is labeled with at least one non-naturally occurring moiety.

2. The composition of claim 1, further comprising at least one ALK fusion gene selected from the group consisting of: EML4 exon 13-ALK exon 20, EML4 exon 20-ALK exon 20, EML4 exon 6a/b-ALK exon 20, EML4 exon 2-ALK exon 20, EML4 exon 18-ALK exon 20, KIF5B exon 17-ALK exon 20, and KIF5B exon 24-ALK exon 20.

3. The composition of claim 1, wherein A includes at least one primer set and probe that amplify and detect more than 2 ALK fusion genes.

4. The composition of claim 2, wherein A includes at least one primer set and probe that amplify and detect EML4 exon 13-ALK exon 20, EML4 exon 20-ALK exon 20, EML4 exon 6a/b-ALK exon 20, EML4 exon 2-ALK exon 20, EML4 exon 18-ALK exon 20, KIF5B exon 17-ALK exon 20, and KIF5B exon 24-ALK exon 20.

5. The composition of claim 1, further comprising at least one RET fusion gene selected from the group consisting of: KIF5B exon 15-RET exon 12, KIF5B exon 16-RET exon 12, KIF5B exon 22-RET exon 12, KIF5B exon 23-RET exon 12, CCDC6 exon 1-RET exon 12, and NCOA4 exon 6-RET exon 12.

6. The composition of claim 1, wherein B includes at least one primer set and probe that amplify and detect more than 2 RET fusion genes.

7. The composition of claim 6, wherein B includes at least one primer set and probe that amplify and detect KIF5B exon 15-RET exon 12, KIF5B exon 16-RET exon 12, KIF5B exon 22-RET exon 12, KIF5B exon 23-RET exon 12, CCDC6 exon 1-RET exon 12, and NCOA4 exon 6-RET exon 12.

8. The composition of claim 1, further comprising at least one ROS1 fusion gene selected from the group consisting of: CD74 exon 6-ROS1 exon 34, CD74 exon 6-ROS1 exon 32, EZR exon 10-ROS1 exon 34, TPM3 exon 8-ROS1 exon 35, SDC4 exon 4-ROS1 exon 34, SDC4 exon 2-ROS1 exon 34, SDC4 exon 2-ROS1 exon 32, SDC4 exon 4-ROS1 exon 32, SLC34A2 exon 13-ROS1 exon 34, SLC34A2 exon 13-ROS1 exon 32v2, SLC34A2 exon 4-ROS1 exon 32, SLC34A2 exon 4-ROS1 exon 35, and LRIG3 exon 16-ROS1 exon 35.

9. The composition of claim 1, wherein C includes at least one primer set and probe that amplify and detect more than 2 ROS1 fusion genes.

10. The composition of claim 9, wherein C includes at least one primer set and probe that amplify and detect CD74 exon 6-ROS1 exon 34, CD74 exon 6-ROS1 exon 32, EZR exon 10-ROS1 exon 34, TPM3 exon 8-ROS1 exon 35, SDC4 exon 4-ROS1 exon 34, SDC4 exon 2-ROS1 exon 32v2, SDC4 exon 2-ROS1 exon 32, SLC34A2 exon 13-ROS1 exon 34, SLC34A2 exon 13-ROS1 exon 32v2, SLC34A2 exon 4-ROS1 exon 32, SLC34A2 exon 4-ROS1 exon 35, and LRIG3 exon 16-ROS1 exon 35.

11. The composition of claim 1, further comprising a thermostable DNA polymerase.

12. The composition of claim 1, further comprising reverse transcriptase.

13. The composition of claim 1, further comprising a biological sample from an individual.

14. The composition of claim 13, wherein the biological sample includes RNA from plasma.

15. A multiplex assay composition comprising:
A. at least one primer set and probe that specifically amplify and detect at least one ALK fusion gene, wherein:
  (i) the at least one primer set that specifically amplifies the at least one ALK fusion gene comprises a forward primer comprising SEQ ID NO:1 and a reverse primer comprising SEQ ID NO:52; and
  (ii) the probe that specifically detects the at least one ALK fusion gene comprises SEQ ID NO:182 and is labeled with at least one non-naturally occurring moiety;
B. at least one primer set and probe that specifically amplify and detect at least one RET fusion gene, wherein:
  (i) the at least one primer set that specifically amplifies the at least one RET fusion gene comprises a forward primer comprising SEQ ID NO:83 and a reverse primer comprising SEQ ID NO:161; and
  (ii) the probe that specifically detects the at least one RET fusion gene comprises SEQ ID NO:189 and is labeled with at least one non-naturally occurring moiety; and
C. a primer set and probe that specifically amplify and detect an internal control, wherein the probe that specifically detects the internal control is labeled with at least one non-naturally occurring moiety.

16. The composition of claim 15, further comprising at least one ALK fusion gene selected from the group consisting of: EML4 exon 13-ALK exon 20, EML4 exon 20-ALK exon 20, EML4 exon 6a/b-ALK exon 20, EML4 exon 2-ALK exon 20, EML4 exon 18-ALK exon 20, KIF5B exon 17-ALK exon 20, and KIF5B exon 24-ALK exon 20.

17. The composition of claim 15 or 16, further comprising at least one RET fusion gene selected from the group consisting of: KIF5B exon 15-RET exon 12, KIF5B exon 16-RET exon 12, KIF5B exon 22-RET exon 12, KIF5B exon 23-RET exon 12, CCDC6 exon 1-RET exon 12, and NCOA4 exon 6-RET exon 12.

18. The composition of claim 15, further comprising a thermostable DNA polymerase.

19. The composition of claim 15, further comprising reverse transcriptase.

20. The composition of claim 15, further comprising a biological sample from an individual.

21. The composition of claim 20, wherein the biological sample includes RNA from plasma.

22. The multiplex assay of claim 1, wherein the label on the probe that detects the internal control is different from the labels on the probes that detect ALK, RET, and ROS1 fusion genes.

23. The multiplex assay of claim 22, wherein the label on the probe that detects the internal control and the labels on the probes that detect ALK, RET, and ROS1 fusion genes are all different from each other.

24. The multiplex assay of claim 1, wherein the labels are each independently selected from a label detectable by a means selected the group consisting of: spectroscopic, photochemical, biochemical, immunochemical, chemical, or physical.

25. The multiplex assay of claim 1, wherein the labels are each independently selected from the group consisting of: fluorophores, quenchers, chromophores, luminescent agents, radioisotopes, electron-dense reagents, and affinity tags.

* * * * *